United States Patent [19]

Schmidt et al.

[11] 4,414,399

[45] Nov. 8, 1983

[54] 5/6 CARBOXYPHTHALIDES

[75] Inventors: Paul J. Schmidt, Sharonville; William M. Hung, Cincinnati, both of Ohio

[73] Assignee: Sterling Drug Inc., New York, N.Y.

[21] Appl. No.: 485,313

[22] Filed: Apr. 15, 1983

Related U.S. Application Data

[60] Division of Ser. No. 281,027, Jul. 6, 1981, which is a continuation-in-part of Ser. No. 135,855, Mar. 31, 1980, Pat. No. 4,298,215, which is a continuation-in-part of Ser. No. 39,017, May 14, 1979, Pat. No. 4,274,660.

[51] Int. Cl.$^3$ ............................................ C07D 307/88
[52] U.S. Cl. ..................................... 549/309; 549/226
[58] Field of Search ......................................... 549/309

[56] References Cited

U.S. PATENT DOCUMENTS 4,104,437  8/1978  Vincent et al. ...................... 549/226

FOREIGN PATENT DOCUMENTS 2242005  3/1973  Fed. Rep. of Germany .
1427318  3/1976  United Kingdom .

*Primary Examiner*—Jane T. Fan
*Attorney, Agent, or Firm*—Terrence E. Miesle; Lynn T. Fletcher; B. Woodrow Wyatt

[57] ABSTRACT

Dialkylamino-substituted 2-anilino-5'/6'-carboxyfluorans, 2-amino and substituted amino-5'-6'-carboxyfluorans, 1,3-dialkyl-5'/6'-carboxyfluorans, esterified dialkylamino-substituted 2-anilino-5'/6'-carboxyfluorans, 2-amino and substituted amino-5'/6'-carboxyfluorans, 1,3-dialkyl-5'/6'-carboxyfluorans and 3,3-(corresponding-substituted-diaryl)-5/6-carboxyphthalides useful as color formers, particularly in carbonless duplicating and thermal marking systems, are prepared by the interaction of 4/5-carboxy-2-(4-dialkylamino-substituted-2-hydroxybenzoyl)benzoic acids and substituted diphenylamines to produce the phthalides which are then subjected to ring closure to produce the carboxyfluorans and by the interaction of 4/5-carboxy-2-(4-dialkylamino-substituted-2-hydroxybenzoyl)benzoid acids and substituted 4-hydroxyacetanilides or alkyl phenols which are esterified with alkyl halides or dialkyl sulfates.

7 Claims, No Drawings

5/6 CARBOXYPHTHALIDES

CROSS REFERENCE TO RELATED APPLICATIONS

This application is a division of our co-pending application Ser. No. 281,027, pending filed July 6, 1981, which in turn is a continuation-in-part of our co-pending application Ser. No. 135,855, filed Mar. 31, 1980 and now U.S. Pat. No. 4,298,215, which in turn is a continuation-in-part of our co-pending application Ser. No. 039,017, filed May 14, 1979 and now U.S. Pat. No. 4,274,660.

BACKGROUND OF THE INVENTION (a) Field of the Invention

This invention relates to novel compounds classified in the field of organic chemistry as fluorans useful as color precursors, particularly in the art of carbonless duplicating, for example, pressure-sensitive and thermal marking systems; to 3,3-(substituted-diaryl)-5/6-carboxyphthalides useful as intermediates to the subject fluoran color precursors; to processes for preparing said fluorans and phthalides; and to pressure-sensitive duplicating systems and thermal marking systems.

(b) Description of the Prior Art

Several classes of organic compounds of widely diverse structural types are well known to be useful as colorless precursors for carbonless duplicating systems. Among the more important classes, there may be named phenothiazines, for example, benzoyl leuco methylene blue; phthalides, for example, crystal violet lactone; fluorans, for example, with which this invention is concerned, for example, 2'-anilino-6'-diethylaminofluoran and 2'-dibenzylamino-6'-diethylaminofluoran; and various other types of colorless precursors currently employed in commercially accepted carbonless copy systems. Typical of the many such systems taught in the prior art are those described in U.S. Pat. Nos. 2,712,507 and 2,800,457 and 3,041,289 which issued July 5, 1955, July 23, 1957 and June 26, 1962, respectively. Many of the color formers in the prior art suffer one or more disadvantages such as low tinctorial strength, poor light stability, low resistance to sublimation, low susceptibility to copiability of the color-developed form in standard copying machines, for example, a Xerox ® copier, and low solubility in common organic solvents, the latter disadvantages thus requiring the use of specialized and expensive solvents in order to obtain microencapsulated solutions of sufficient concentration for use in pressure-sensitive copying systems.

The following items to date appear to constitute the most relevant prior art with regard to the instant invention.

U.S. Pat. No. 4,104,437, issued Aug. 1, 1978, discloses and claims a pressure-sensitive copy system bearing pressure-rupturable microcapsules containing a chromogenic compound having the formula

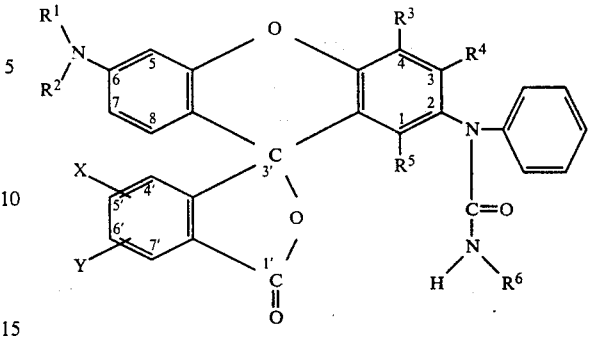

and containing additionally in admixture a chromogenic precursor having the formula

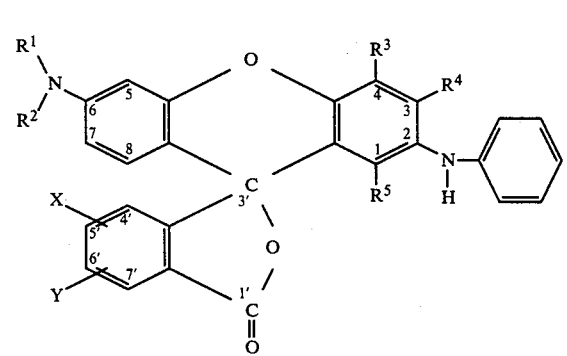

wherein $R^1$ and $R^2$ each represent an alkyl group; $R^3$ and $R^4$ each represent a hydrogen atom; a halogen atom, an alkyl group, a nitro group, an amino group, an acyl group, or a carboalkoxy group; $R^5$ represents a hydrogen atom or an alkyl group, with the proviso that $R^5$ represents an alkyl group only when $R^4$ represents a hydrogen atom; $R^6$ represents an alkyl group, an aryl group or an aralkyl group; and X and Y each represent a hydrogen atom, a halogen atom, a nitro group, a lower alkyl group, an aryl group, an alkoxy group, or a carboalkoxy group.

British Pat. No. 1,427,318, issued Mar. 10, 1976, discloses a fluoran having the formula

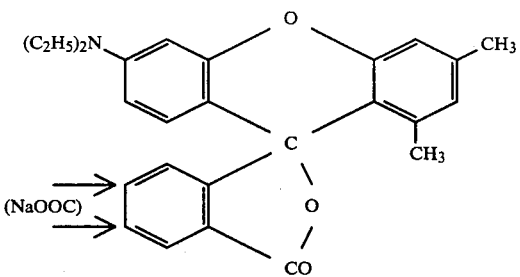

German Offenlegungsschrift No. 2,242,005 which was published Mar. 15, 1973, discloses a process for the preparation of phthalides of the formula

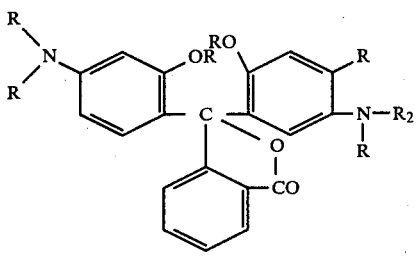

by interacting a 2-hydroxy or alkoxy-4-dialkylamino-2'-carboxybenzophenone with a phenol of the formula

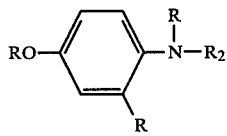

wherein R is hydrogen or alkyl and $R_2$ is hydrogen, phenyl or phenyl substituted by alkyl in the presence of sulfuric acid at 10°–30° C. for 2–5 hours and then making alkaline to pH 8–10.5 to isolate the phthalide. Alternatively, by adjusting the pH to 10–11, heating the alkaline reaction mixture at 80°–100° C., the corresponding fluorans are formed. The compounds have disclosed utility as color formers for pressure-sensitive papers.

SUMMARY OF THE INVENTION

The present invention provides for novel fluorans selected from among substituted 2-anilino-5'/6'-carboxyfluorans, 2-amino-5'/6'-carboxyfluorans, 1,3-dialkyl-5'/6'-carboxyfluorans, 2-anilino-5'/6'-alkoxycarbonylfluorans, 2-anilino-5'/6'-phenylmethoxycarbonylfluorans, 2-acetamido-5'/6'-alkoxycarbonylfluorans, 2-dialkylamino-5'/6'-alkoxycarbonylfluorans, 2-dialkylamino-5'/6'-phenylmethoxycarbonylfluorans, 2-pyrrolyl-5'/6'-alkoxycarbonylfluorans, 2-pyrrolyl-5'/6'-phenylmethoxycarbonylfluorans, 1,3-dialkyl-5'/6'-alkoxycarbonylfluorans, 1,3-dialkyl-5'/6'-phenylmethoxycarbonylfluorans which are useful as color formers in pressure-sensitive duplicating systems and in thermal marking systems. The compounds develop colored images of good to excellent tinctorial strength, and have the advantages of good light stability and enhanced solubility in common organic solvents. The present invention also provides 3,3-(substituted diaryl)-5/6-carboxyphthalides useful as intermediates to the subject fluoran color formers which are also useful as color formers for thermal marking systems.

In one of its composition of matter aspects the invention relates to a series of 1-$R^o$-2-$R^4$-3-$R^1$-6-$(R)_2$-amino-5'/6'-Y-carbonylfluorans which are useful as color formers in pressure-sensitive carbonless duplicating systems and thermal marking systems.

In a second of it composition of matter aspects, the invention relates to a series of 3-[2-hydroxy-4-$(R)_2$aminophenyl]-3-(2-$R^3$-4-$R^1$-5-$R^4$)-5/6-carboxyphthalides which are useful as intermediates for the preparation of the fluoran final products of the invention and which are also useful as color formers for thermal marking systems.

In one of its process aspects, the invention relates to a process for preparing 2-anilino-3-$R^1$-6-$(R)_2$amino-5'/6'-carboxyfluoran which comprises heating a 3-[2-hydroxy-4-$(R)_2$aminophenyl]-3-(2-$R^3$-4-$R^1$-5-anilinophenyl)-5/6-carboxyphthalide in the presence of an alkali metal hydroxide.

In a second of its process aspects, the invention relates to a process for preparing 2-anilino-3-$R^1$-6-$(R)_2$amino-5'/6'-alkoxycarbonyl- or phenylmethoxycarbonylfluorans which comprises esterifying the corresponding 2-anilino-3-$R^1$-6-$(R)_2$amino-5'/6'-carboxyfluoran with an appropriate alkylating agent in the presence of an alkali.

In a third process aspect, the invention relates to a process for preparing a 3-[2-hydroxy-4-$(R)_2$aminophenyl]-3-(2-$R^3$-4-$R^1$-5-anilinophenyl)-5/6-carboxyphthalide which comprises interacting the appropriate 4/5-carboxy-2-[4-$(R)_2$amino-2-hydroxybenzoyl]benzoic acid with the appropriate 2-$R^1$-4-$R^3$-diphenylamine in the presence of sulfuric acid.

In a fourth of its process aspects, the invention relates to a process for preparing 2-$R^{4'}$-3-$R^1$-6-$(R)_2$-amino-5'/6'-carboxyfluorans which comprises heating a 3-[2-hydroxy-4-$(R)_2$-aminophenyl]-3-(2-$R^3$-4-$R^1$-5-$R^{4'}$-phenyl)-5/6-carboxyphthalide in the presence of an alkali metal hydroxide or carbonate.

In a fifth of its process aspects, the invention relates to a process for preparing 2-$R'$-3-$R^1$-6$(R)_2$-amino-5'/6'-$R^2O$-carbonylfluorans which comprises esterifying the corresponding 2-$R^{4'}$-3-$R^1$-6-$(R)_2$-amino-5'/6'-carboxyfluoran with an appropriate alkylating agent in the presence of an alkali.

In a sixth of its process aspects, the invention relates to the process for preparing 3-[2-hydroxy-4-$(R)_2$-amino-phenyl]-3-(2-$R^3$-4-$R^1$-5-$R^{4'}$-phenyl)-5/6-carboxyphthalides which comprises interacting a 4/5-carboxy-2-[4-$(R)_2$-amino-2-hydroxybenzoyl]benzoic acid with approximately one molecular proportion of a 2-$R^1$-4-$R^3$-N-$R^{4'}$-aniline in the presence of sulfuric acid.

In a seventh process aspect, the invention relates to a process for preparing a 2-amino-3-$R^1$-6-$(R)_2$-amino-5'/6'-carboxyfluoran which comprises, in a first step, interacting the appropriate 4/5-carboxy-2-[4-$(R)_2$-amino-2-hydroxybenzoyl]benzoic acid with the appropriate 2-$R^1$-4-hydroxyacetanilide in the presence of sulfuric acid, and in a second step, heating the product formed in step one in the presence of an alkali metal hydroxide.

In an eighth process aspect the invention relates to a process for preparing 2-$(R^5)(R^{6'})$-amino-3-$R^1$-6-$(R)_2$-amino-5'/6'-alkoxycarbonyl- or phenylmethoxycarbonylfluorans which comprises esterifying the corresponding 2-amino-3-$R^1$-6-$(R)_2$-amino-5'/6'-carboxyfluoran with an appropriate alkylating agent in the presence of an alkali.

In a ninth process aspect, the invention relates to a process for preparing a 2-acetamido-3-$R^1$-6-$(R)_2$-amino-5'/6'-carboxyfluoran which comprises interacting the appropriate 4/5-carboxy-2-[4-$(R)_2$-amino-2-hydroxybenzoyl]benzoic acid with the appropriate 2-$R^1$-4-hydroxyacetanilide in the presence of sulfuric acid.

In a tenth process aspect, the invention relates to a process for preparing 2-acetamido-3-$R^1$-6-$(R)_2$-amino-5'/6'-alkoxycarbonyl- or phenylmethoxycarbonylfluorans which comprises esterifying the corresponding 2-acetamido-3-$R^1$-6-$(R)_2$-amino-5'/6'-carboxyfluoran with an appropriate alkylating agent in the presence of an alkali.

In an eleventh process aspect, the invention relates to a process for preparing a 2-(1-pyrrolyl)-3-$R^1$-6-$(R)_2$- amino-5'/6'-carboxyfluoran which comprises interacting 2-amino-3-$R^1$-6-$(R)_2$-amino-5'/6'-carboxyfluoran with 2,5-dialkoxytetrahydrofuran in the presence of an acid.

In a twelfth process aspect, the invention relates to a process for preparing a 2-(2,5-dimethyl-1-pyrrolyl)-3-$R^1$-6-$(R)_2$-amino-5'/6'-carboxyfluoran which comprises interacting an appropriate 2-amino-3-$R^1$-6-$(R)_2$-amino-5'/6'-carboxyfluoran with 2,5-hexanedione in the presence of an acid.

In a thirteenth process aspect, the invention relates to a process for preparing a 2-[2,5-$(R^7)_2$-1-pyrrolyl]-3-$R^1$-6-$(R)_2$-amino-5'/6'-alkoxycarbonyl- or phenylmethoxycarbonylfluoran which comprises esterifying the corresponding 2-[2,5-$(R^7)_2$-1-pyrrolyl]-3-$R^1$-6-$(R)_2$-amino-5'/6'-carboxyfluoran with an appropriate alkylating agent in the presence of an alkali.

In a fourteenth process aspect, the invention relates to a process for preparing a 1-$R^o$-3-$R^1$-6-$(R)_2$-amino-5'/6'-carboxyfluoran which comprises interacting 4/5-carboxy-2-[4-$(R)_2$-amino-2-hydroxybenzoyl]benzoic acid with an appropriate 3-$R^o$-5-$R^1$-1-phenol in the presence of sulfuric acid.

In a fifteenth process aspect, the invention relates to a process for preparing 1-$R^o$-3-$R^1$-6-$(R)_2$-amino-5'/6'-alkoxycarbonyl- or phenylmethoxycarbonylfluorans which comprises esterifying the appropriate 1-$R^o$-3-$R^1$-6-$(R)_2$-amino-5'/6'-carboxyfluoran with an appropriate alkylating agent in the presence of an alkali.

The present invention provides in one of its article of manufacture aspects, pressure-sensitive carbonless duplicating systems and thermal marking systems each containing at least one color-forming substance comprising a 2-anilino-3-$R^1$-6-$(R)_2$-amino-5'/6'-Y-carbonylfluoran.

In a second article of manufacture aspects, the invention relates to thermal marking systems each containing at least one color-forming substance comprising a 3-[2-hydroxy-4-$(R)_2$-aminophenyl]-3-(2-$R^3$-4-$R^1$-5-anilinophenyl)-5/6-Y-carbonylphthalide.

In a third article of manufacture aspects, the invention relates to pressure-sensitive carbonless duplicating systems and thermal marking systems each containing at least one color-forming substance comprising a 1-$R^o$-2-$R^{4'}$-3-$R^1$-6-$(R)_2$-amino-5'/6'-Y-carbonylfluoran.

DETAILED DESCRIPTION INCLUSIVE OF THE PREFERRED EMBODIMENTS

More specifically, this invention in one of its composition of matter aspects relating to final products, resides in the novel fluorans, which are particularly useful as colorless precursors in the art of carbonless duplicating and thermal marking, and which are selected from the group consisting of 1-$R^o$-2-$(R^4)$-3-$R^1$-6-$(R)_2$-amino-5'/6'-Y-carbonylfluoran having the formula

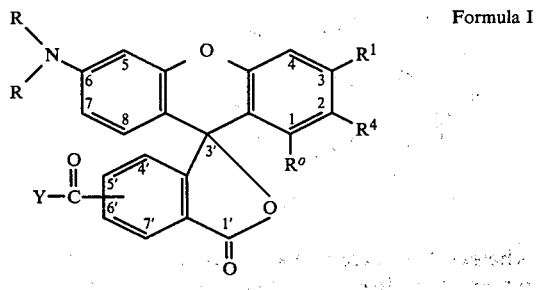

Formula I wherein R represents a non-tertiary $C_1$ to $C_4$ alkyl; $R^o$ and $R^1$ each represent hydrogen or a non-tertiary $C_1$ to $C_4$ alkyl; $R^4$ represents hydrogen or -$N(R^5)(R^6)$ in which $R^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy; $R^6$ represents hydrogen, phenyl, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy or acyl, or $R^5$ and $R^6$ taken together with the nitrogen represent 2,5-$(R^7)_2$-1-pyrrolyl in which $R^7$ represents non-tertiary hydrogen or $C_1$ to $C_4$ alkyl; Y represents $OR^2$ in which $R^2$ represents hydrogen, a non-tertiary $C_1$ to $C_{18}$ alkyl, benzyl or benzyl substituted by halo, nitro, a non-tertiary $C_1$ to $C_4$ alkyl or a non-tertiary $C_1$ to $C_4$ alkoxy, alkali metal cation or ammonium cation.

In a first particular embodiment in accordance with its first product composition of matter aspect, the invention sought to be patented resides in the novel 2-anilino-3-$R^1$-6-$(R)_2$-amino-5'/6'-Y-carbonylfluoran having the formula

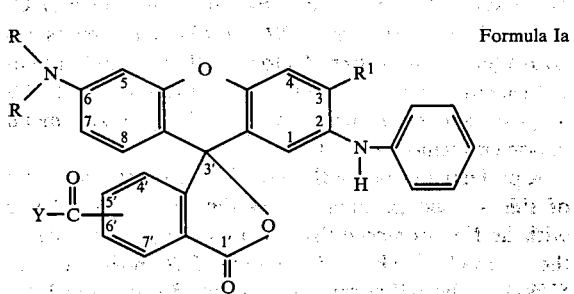

Formula Ia wherein R represents a non-tertiary $C_1$ to $C_4$ alkyl; $R^1$ represents hydrogen or a non-tertiary $C_1$ to $C_4$ alkyl; and Y represents $OR^2$ in which $R^2$ represent hydrogen, a non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkyl, alkali metal cation or ammonium cation.

A preferred group of fluorans falling within the ambit of this first particular embodiment in accordance with its first composition of matter aspect resides in the novel 2-anilino-3-$R^1$-6-$(R)_2$-amino-5'/6'-carboxyfluorans of Formula Ia wherein Y is OH and R and $R^1$ each have the same respective meanings given in Formula Ia.

Another preferred group of fluorans falling within the ambit of the first particular embodiment in accordance with its first compoosition of matter aspect resides in the novel 2-anilino-3-$R^1$-6-$(R)_2$-amino-5'/6'-$R^2O$-carbonylfluorans of Formula Ia wherein Y is $R^2O$ and $R^2$ represents non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and R and $R^1$ each have the same respective meanings given in relation to Formula Ia.

In a second particular embodiment in accordance with its first composition of matter aspect, the invention sought to be patented resides in the novel 1-$R^o$-2-$R^{4'}$-3-$R^1$-6-$(R)_2$-amino-5'/6'-Y-carbonylfluoran of the formula

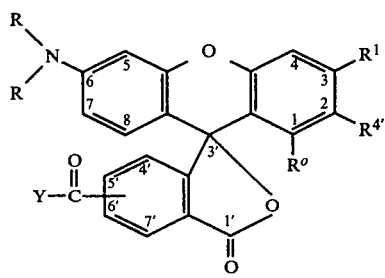

Formula Ib

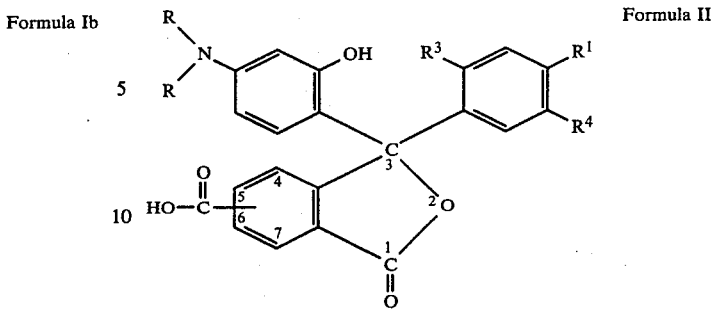

Formula II wherein R represents a non-tertiary $C_1$ to $C_4$ alkyl; $R^o$ and $R^1$ each represent hydrogen or a non-tertiary $C_1$ to $C_4$ alkyl; $R^{4'}$ represents $-N(R^5)(R^{6'})$ in which $R^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy, $R^{6'}$ represents hydrogen, non-tertiary $C_1$ to $C_{18}$ alkyl, benzyl, benzyl substituted by halo, nitro, non-tertiary $C_1$ to $C_4$ alkyl or non-tertiary $C_1$ to $C_4$ alkoxy or acyl, or $R^5$ and $R^{6'}$ taken together with the nitrogen represent 2,5-$(R^7)_2$-1-pyrrolyl in which $R^7$ represents non-tertiary hydrogen or $C_1$ to $C_4$ alkyl; Y represents $OR^2$ in which $R^2$ represents hydrogen, a non-tertiary $C_1$ to $C_{18}$ alkyl, benzyl or benzyl substituted by halo, nitro, a non-tertiary $C_1$ to $C_4$ alkyl or a non-tertiary $C_1$ to $C_4$ alkoxy, alkali metal cation or ammonium cation.

A preferred group of fluorans falling within the ambit of this second particular embodiment in accordance with its first compoosition of matter aspect resides in the novel 2-$(R^5)$ $(R^{6'})$-amino-3-$R^1$-6-$(R)_2$-amino-5'/6'-Y-carbonylfluorans of Formula Ib wherein $R^o$ is hydrogen and $R^{4'}$ is $-N(R^5)(R^{6'})$ and $R^5$ and $R^{6'}$ each independently represent hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and R, $R^1$ and Y each have the same respective meanings given in Formula IB.

Another preferred group of fluorans falling within the ambit of this second particular embodiment in accordance with its first composition of matter aspect resides in the novel 2-[2,5-$(R^7)_2$-1-pyrrolyl]-3-$R^1$-6-$(R)_2$-amino-5'/6'-Y-carbonylfluorans of Formula Ib wherein $R^o$ is hydrogen and $R^{4'}$ is 2,5-$(R^7)_2$-1-pyrrolyl and $R^7$ represents hydrogen or $C_1$ to $C_4$ alkyl and R, $R^1$ and Y each have the same respective meanings given in Formula Ib.

Still another preferred group of fluorans falling within the ambit of this second particular embodiment in accordance with its first composition of matter aspect resides in the novel 1-$R^o$-3-$R^1$-6-$(R)_2$-amino-5'/6'-Y-carbonylfluoran of Formula Ib wherein $R^o$ and $R^1$ each represent $C_1$ to $C_4$ alkyl, $R^4$ represents hydrogen and R and Y each have the same respective meaning given in Formula Ib.

This invention, in a second of its composition of matter aspects, relating to intermediates to the fluorans and to final products useful as color formers in thermal marking systems, resides in the novel 3-[2-hydroxy-4-$(R)_2$-aminophenyl]-3-(2-$R^3$-4-$R^1$-5-$R^4$-phenyl)-5/6-carboxyphthalides having the formula wherein: R represents a non-tertiary $C_1$ to $C_4$ alkyl; $R^1$ represents hydrogen or a non-tertiary $C_1$ to $C_4$ alkyl; $R^3$ represents a non-tertiary $C_1$ to $C_4$ alkoxy; and $R^4$ represents $N(R^5)(R^6)$ in which $R^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy; and $R^6$ represents hydrogen, phenyl, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy or acyl.

In a first particular embodiment in accordance with its second composition of matter aspect, the invention sought to be patented resides in the novel 3-[2-hydroxy-4-$(R)_2$-aminophenyl]-3-(2-$R^3$-4-$R^1$-5-anilinophenyl)-5/6-carboxyphthalides having the formula

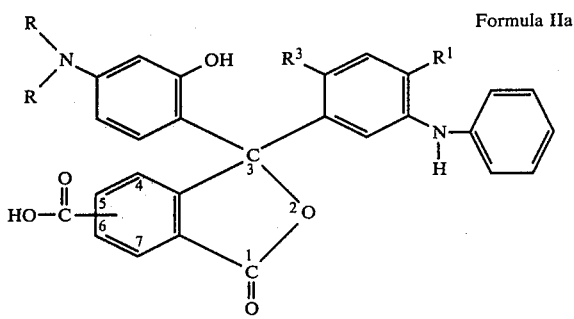

Formula IIa wherein: R represents non-tertiary $C_1$ to $C_4$ alkyl; $R^1$ represents hydrogen or a non-tertiary $C_1$ to $C_4$ alkyl; and $R^3$ represents a non-tertiary $C_1$ to $C_4$ alkoxy.

In a second particular embodiment in accordance with its second composition of matter aspect, the invention sought to be patented resides in the novel 3-[2-hydroxy-4-$(R)_2$-aminophenyl]-3-(2-$R^3$-4-$R^1$-5-$R^{4'}$-phenyl)-5/6-carboxyphthalides having the formula

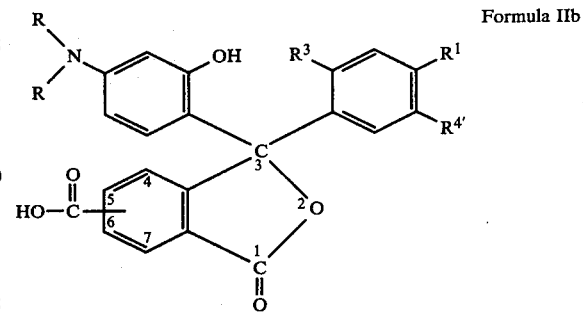

Formula IIb wherein: R represents a non-tertiary $C_1$ to $C_4$ alkyl; $R^1$ represents hydrogen or a non-tertiary $C_1$ to $C_4$ alkyl; $R^3$ represents a non-tertiary $C_1$ to $C_4$ alkoxy; and $R^{4'}$ represents $-N(R^5)(R^{6'})$, in which $R^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy, $R^{6'}$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy or acyl.

In one of its process aspects, the invention sought to be patented resides in a process for preparing a 2-anilino-3-$R^1$-6-$(R)_2$-amino-5'/6'-carboxyfluoran according to Formula Ia which comprises heating a 3-[2-hydroxy-4-$(R)_2$-aminophenyl]-3-(2-$R^3$-4-$R^1$-5-anilinophenyl)-5/6-carboxyphthalide of Formula IIa in the presence of an alkali metal hydroxide to effect ring closure wherein $R^3$ represents a non-tertiary $C_1$ to $C_4$ alkoxy and R and $R^1$ each have the same respective meanings given in relation to Formula Ia.

In a second of its process aspects, the invention sought to be patented resides in the process for preparing a 2-anilino-3-$R^1$-6-$(R)_2$-amino-5'/6'-$R^2$O-carbonylfluorans according to Formula Ia wherein $R^2$ represents a non-tertiary $C_1$ to $C_{18}$ alkyl or benzyl and wherein R and $R^1$ each have the same respective meanings given in relation to Formula Ib which comprises esterifying the corresponding 2-anilino-3-$R^1$-6-$(R)_2$-amino-5'/6'-carboxyfluoran with an appropriate compound selected from the group consisting of dimethylsulfate, diethyl sulfate or $R^2$-halogen in which $R^2$ is non-tertiary $C_1$ to $C_{18}$ alkyl or benzyl in the presence of an alkali metal hydroxide or carbonate.

In a third of its process aspects, the invention sought to be patented resides in the process for preparing a 3-[2-hydroxy-4-$(R)_2$-aminophenyl]-3-(2-$R^3$-4-$R^1$-5-anilinophenyl)-5/6-carboxyphthalide according to Formula IIa which comprises interacting a 4/5-carboxy-2-[4-$(R)_2$-amino-2-hydroxybenzoyl]benzoic acid with approximately one molecular proportion of a 2-$R^1$-4-$R^3$-diphenylamino in the presence of sulfuric acid wherein R, $R^1$ and $R^3$ each have the same meanings given in relation to Formula IIa.

In a fourth of its process aspects, the invention sought to be patented resides in a process for preparing a 2-$R^{4'}$-3-$R^1$-6-$(R)_2$-amino-5'/6'-carboxyfluoran according to Formula Ib which comprises heating a 3-[2-hydroxy-4-$(R)_2$-aminophenyl]-3-(2-$R^3$-4-$R^1$-5-$R^{4'}$-phenyl)-5/6-carboxyphthalide of Formula IIb in the presence of an alkali metal hydroxide or carbonate to effect ring closure wherein $R^3$ represents a non-tertiary $C_1$ to $C_4$ alkoxy and R, $R^1$ and $R^{4'}$ each have the same respective meanings given in relation to Formula Ib.

In a fifth of its process aspects, the invention sought to be patented resides in the process for preparing a 2-$R^{4'}$-3-$R^1$-6-$(R)_2$-amino-5'/6'-$R^2$O-carbonylfluoran according to Formula Ib wherein $R^2$ represents a non-tertiary $C_1$ to $C_{18}$ alkyl or benzyl and wherein R, $R^1$ and $R^{4'}$ each have the same respective meanings given in relation to Formula Ib which comprises esterifying the corresponding 2-$R^{4'}$-3-$R^1$-6-$(R)_2$-amino-5'/6'-carboxyfluoran with an appropriate compound selected from the group consisting of dimethylsulfate, diethyl sulfate or $R^2$-halogen in which $R^2$ is non-tertiary $C_1$ to $C_{18}$ alkyl or benzyl in the presence of an alkali metal hydroxide or carbonate.

In a sixth of its process aspects, the invention sought to be patented resides in the process for preparing a 3-[2-hydroxy-4-$(R)_2$-aminophenyl]-3-(2-$R^3$-4-$R^1$-5-$R^{4'}$-phenyl)-5/6-carboxyphthalide according to Formula IIb which comprises interacting a 4/5-carboxy-2-[4-$(R)_2$-amino-2-hydroxybenzoyl]benzoic acid with approximately one molecular proportion of a 2-$R^1$-4-$R^3$-N-$R^{4'}$-aniline in the presence of sulfuric acid wherein R, $R^1$ and $R^3$ each have the same meanings given in relation to Formula IIb.

In a seventh of its process aspects, the invention sought to be patented resides in the process for preparing a 2-amino-3-$R^1$-6-$(R)_2$-amino-5'/6'-carboxyfluoran according to Formula I wherein $R^4$ represents $-N(R^5)(R^6)$ in which $R^5$ and $R^6$ each represent hydrogen, $R^o$ represents hydrogen, and Y represents OH and wherein R and $R^1$ each have the same respective meanings given in relation to Formula I which comprises, in a first step, interacting a 4/5-carboxy-2-[4-$(R)_2$-amino-2-hydroxybenzoyl]benzoic acid with approximately one molecular proportion of 2-$R^1$-4-hydroxyacetanilide in the presence of sulfuric acid and, in a second step, the intermediate from step one without isolation is heated in its presence of an alkali metal hydroxide.

In an eighth of its process aspects, the invention sought to be patented resides in the process for preparing a 2-$(R^5)(R^6)$-amino-3-$R^1$-6-$(R)_2$-amino-5'/6'-$R^2$O-carbonylfluoran according to Formula I wherein $R^o$ represents hydrogen, $R^4$ represents $-N(R^5)(R^6)$ and Y represents $R^2$O- in which $R^2$, $R^5$ and $R^6$ each represent non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and R and $R^1$ each have the same respective meanings given in Formula I which comprises esterifying the corresponding 2-amino-3-$R^1$-6-$(R)_2$-amino-5'/6'-carboxyfluoran with an appropriate compound selected from the group consisting of dimethylsulfate, diethylsulfate or $R^2$-halogen in which $R^2$ is non-tertiary $C_1$ to $C_{18}$ alkyl, benzyl or benzyl substituted by halo, nitro, non-tertiary $C_1$ to $C_4$ alkoxy in the presence of an alkali metal hydroxide or carbonate.

In a ninth of its process aspects, the invention sought to be patented resides in the process for preparing a 2-acetamido-3-$R^1$-6-$(R)_2$-amino-5'/6'-carboxyfluoran according to Formula I wherein $R^o$ represents hydrogen, $R^4$ represents $-N(R^5)(R^6)$ in which $R^5$ represents hydrogen and $R^6$ represents acetyl and Y represents OH and wherein R and $R^1$ each have the same respective meanings given in Formula I which comprises interacting a 4/5-carboxy-2-[4-$(R)_2$-amino-2-hydroxybenzoyl]benzoic acid with approximately one molecular proportion of a 2-$R^1$-4-hydroxy-1-acetanilide in the presence of sulfuric acid.

In a tenth of its process aspects, the invention sought to be patented resides in the process for preparing a 2-acetamido-3-$R^1$-6-$(R)_2$-amino-5'/6'-$R^2$O-carbonylfluoran according to Formula I wherein $R^o$ represents hydrogen, $R^4$ represents $-N(R^5)(R^6)$ in which $R^5$ represents hydrogen and $R^6$ represents acetyl and Y represents $R^2$O- in which $R^2$ represents a non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and wherein R and $R^1$ each have the same respective meanings given in Formula I which comprises esterifying the corresponding 2-acetamido-3-$R^1$-6-$(R)_2$-amino-5'/6'-carboxyfluoran with an appropriate compounds selected from the group consisting of dimethylsulfate, diethylsulfate or $R^2$-halogen in which $R^2$ is non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy in the presence of an alkali metal hydroxide or carbonate.

In an eleventh of its process aspects, the invention sought to be patented resides in the process for preparing a 2-(1-pyrrolyl)-3-$R^1$-6-$(R)_2$-amino-5'/6'-carboxyfluoran according to Formula I wherein $R^o$ represents hydrogen, $R^4$ represents $-N(R^5)(R^6)$ in which $R^5$ and $R^6$ taken together with the nitrogen form pyrrolyl, Y represents OH and R and $R^1$ each have the same respective meanings given in Formula I which comprises interacting 2-amino-3-$R^1$-6-$(R)_2$-amino-5'/6'-carboxyfluoran with 2,5-dialkoxytetrahydrofuran in the presence of an acid.

In a twelfth of its process aspects, the invention sought to be patented resides in the process for preparing a 2-(2,5-dimethyl-1-pyrrolyl)-3-$R^1$-6-$(R)_2$-amino-5'/6'-carboxyfluoran according to Formula I wherein $R^o$ represents hydrogen, $R^4$ represents $-N(R^5)(R^6)$ in which $R^5$ and $R^6$ taken together with the nitrogen atom represents 2,5-$(R^7)_2$-1-pyrrolyl in which $R^7$ represents methyl, Y represents OH and wherein R and $R^1$ each have the same respective meanings given in Formula I which comprises interacting 2-amino-3-$R^1$-6-$(R)_2$-amino-5'/6'-carboxyfluoran with 2,5-hexanedione in the presence of an acid.

In a thirteenth of its process aspects, the invention sought to be patented resides in the process for preparing a 2-[2,5-$(R^7)_2$-pyrrolyl]-3-$R^1$-6-$(R)_2$-amino-5'/6'-$R^2$O-carbonylfluoran according to Formula I wherein $R^o$ represents hydrogen, $R^4$ represents $-N(R^5)(R^6)$ in which $R^5$ and $R^6$ taken together with the nitrogen atom represent 2,5-$(R^7)_2$-1-pyrrolyl and $R^2$ represents a non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and wherein R and $R^1$ each represent the same respective meanings given in Formula I which comprises esterifying the corresponding 2-[2,5-$(R^7)_2$-1-pyrrolyl]-3-$R^1$-6-$(R)_2$-amino-5'/6'-carboxyfluoran with an appropriate compound selected from the group consisting of dimethyl sulfate, diethyl sulfate or $R^2$-halogen in which $R^2$ is non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy in the presence of an alkali metal carbonate.

In a fourteenth of its process aspects, the invention sought to be patented resides in the process for preparing a 1-$R^o$-3-$R^1$-6-$(R)_2$-amino-5'/6'-carboxyfluoran according to Formula I wherein $R^4$ represents hydrogen and Y represents OH and wherein R, $R^o$ and $R^1$ each have the same respective meanings given in Formula I which comprises interacting a 4/5-carboxy-2-[4-$(R)_2$-amino-2-hydroxybenzoyl]benzoic acid with approximately one molecular proportion of a 3-$R^o$-5-$R^1$-1-phenol in the presence of sulfuric acid.

In a fifteenth of its process aspects, the invention sought to be patented resides in the process for preparing a 1-$R^o$-3-$R^1$-6-$(R)_2$-amino-5'/6'-$R^2$O-carbonylfluoran according to Formula I wherein $R^4$ represents hydrogen, Y represents $R^2$O in which $R^2$ represents non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy and wherein R, $R^o$ and $R^1$ each have the same respective meanings given in Formula I which comprises esterifying the corresponding 1-$R^o$-3-$R^1$-6-$(R)_2$-amino-5'/6'-carboxyfluoran with an appropriate compound selected from the group consisting of dimethyl sulfate, diethyl sulfate or $R^2$-halogen in which $R^2$ is non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy in the presence of an alkali metal carbonate.

In an article of manufacture aspect, the invention sought to be patented resides in a pressure-sensitive or thermal marking system containing as a color-forming substance a 2-anilino-3-$R^1$-6-$(R)_2$amino-5'/6'-Y-carbonylfluoran according to Formula Ia wherein R, $R^1$ and Y each have the same respective meanings given relative to Formula Ia.

In a particular embodiment in accordance with its first article of manufacture aspect, the invention sought to be patented resides in a pressure-sensitive transfer sheet, adapted for use with a receiving sheet having an electron accepting layer, comprising a support sheet coated on one side with a layer of pressure-rupturable microcapsules, said microcapsules containing a liquid solution of a color-forming substance comprising at least one compound having Formula Ia.

Another particular embodiment in accordance with its first article of manufacture aspect, resides in a heat responsive record material comprising a support sheet coated on one side with a layer containing a mixture comprising at least one color-forming compound having Formula Ia and an acidic developer arranged such that application of heat will produce a mark-forming reaction between the color-forming compound and the acidic developer.

Preferred articles within the ambit of the particular embodiments above-described are those wherein the color-forming component comprises a 2-anilino-3-$R^1$-6-$(R)_2$-amino-5'/6'-$R^2$O-carbonylfluoran according to Formula Ia in which Y is $R^2$O wherein R, $R^1$ and $R^2$ each have the same respective meanings given in relation to Formula Ia.

In a second article of manufacture aspect, the invention sought to be patented resides in a thermal marking system containing as a color-forming substance a 3-[2-hydroxy-4-$(R)_2$-aminophenyl]-3-(2-$R^3$-4-$R^1$-5-anilinophenyl)-5/6-carboxyphthalide according to Formula II wherein R, $R^1$ and $R^3$ each have the same respective meanings given in relation to Formula II.

In a particular embodiment in accordance with its second article of manufacture aspect, the invention resides in a heat responsive record material comprising a support sheet coated on one side with a layer containing a mixture comprising at least one color-forming compound having Formula II and an acidic developer arranged such that application of heat will produce a mark-forming reaction between the color-forming compound and the acidic developer.

In a third article of manufacture aspect, the invention sought to be patented resides in a pressure-sensitive or thermal marking system containing as a color-forming substance a 1-$R^o$-2-$R^{4'}$-3-$R^1$-6-$(R)_2$amino-5'/6'-Y-carbonylfluoran according to Formula Ib wherein R, $R^o$, $R^1$, $R^{4'}$ and Y each have the same respective meanings given in Formula Ib.

In particular embodiment in accordance with its third article of manufacture aspect, the invention sought to be patented resides in a pressure-sensitive transfer sheet, adapted for use with a receiving sheet having an electron accepting layer, comprising a support sheet coated on one side with a layer of pressure-rupturable microcapsules, said microcapsules containing a liquid solution of a color-forming substance comprising at least one compound having Formula Ib.

Another particular embodiment in accordance with its third article of manufacture aspect, resides in a heat responsive record material comprising a support sheet coated on one side with a layer containing a mixture comprising at least one color-forming compound having Formula Ib and an acidic developer arranged such that application of heat will produce a mark-forming reaction between the color-forming compound and the acidic developer.

Preferred articles within the ambit of the particular embodiments above-described are those wherein the color-forming component comprises a 1-$R^o$-2-$R^{4'}$-3-$R^1$-6-$(R)_2$amino-5'/6'-$R^2$O-carbonylfluoran according to Formula Ib in which Y is $R^2$O wherein R, $R^o$, $R^1$, $R^2$ and $R^{4'}$ each have the same respective meanings given in relation to Formula Ib.

As used herein the terms "non-tertiary $C_1$ to $C_4$ alkyl", and "non-tertiary $C_1$ to $C_{18}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl, n-tridecyl, n-tetradecyl, n-pentadecyl, n-hexadecyl, n-heptadecyl, n-octadecyl, 1,3,5-trimethylhexyl, 1,5-dimethyl-4-ethylhexyl, 5-methyl-2-butylhexyl, 2-propylnonyl, 2-butyloctyl, 2-pentylnonyl, 1,2-dimethylhexadecyl, and the like.

As used herein the term "alkali metal cation" includes lithium, sodium and potassium cations.

The term "non-tertiary $C_1$ to $C_4$" alkoxy includes saturated, acyclic, straight or branched-chained groups such as methoxy, ethoxy, propoxy, isopropoxy, butoxy, sec-butoxy and isobutoxy.

As used herein the term "halo" includes fluoro, chloro, bromo and iodo.

The novel compounds of Formula I hereinabove are essentially colorless in the depicted form. When contacted with an acidic medium, for example, silica gel or one of the types ordinarily employed in pressure-sensitive carbonless duplicating systems such as silton clay or phenolic resins the compounds of Formula I develop a red through green to a black-colored image of good to excellent tinctorial strength, and possessing excellent light stability, resistance to sublimation and xerographic copiability. The compounds are thus highly suitable for use as colorless precursors, that is color-forming substances in pressure-sensitive carbonless duplicating systems. The black colors can be used alone as color formers to produce images which are readily copiable, whereas the green colors can be used as toners in admixture with other color formers to produce images of a neutral shade which desirably are readily copiable by xerographic means. Moreover, the compounds of Formula I, in particular those wherein $R^2$ represents $C_1$ to $C_{18}$ alkyl have enhanced solubility in common and inexpensive organic solvents such as odorless mineral spirits, kerosene, vegetable oils and the like thereby avoiding the need for more expensive, specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such applications is as follows. Solutions containing one or more colorless precursor compounds of Formula I, optionally in admixture with other color formers, in suitable solvents are microencapsulated by well-known procedures for example as described in U.S. Pat. No. 3,649,649. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms red through green to black-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formulas I and II are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from green to black depending on the particular compound of the invention employed. The ability of the compounds of Formulas I and II to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with one of the process aspects of this invention the 3-[2-hydroxy-4-$(R)_2$aminophenyl]-3-(2-$R^3$-4-$R^1$-5-$R^4$-phenyl)-5/6-carboxyphthalides of Formula II are obtained by interacting in approximately equimolecular proportions an appropriate 4/5-carboxy-2-[4-$(R)_2$amino-2-hydroxybenzoyl]benzoic acid with an appropriate 2-$R^1$-4-$R^3$-N-$R^4$-aniline. The reaction is conveniently carried out in a dehydrating solvent, for example, a mixture of 100 percent sulfuric acid and oleum at a temperature in the approximate range of 0°–35° C. for from approximately two to approximately six hours. The 3-[2-hydroxy-4-$(R)_2$aminophenyl]-3-(2-$R^3$-4-$R^1$-5-$R^4$-phenyl)-5/6-carboxyphthalide thus obtained are isolated by adding the reaction mixture to ice-water and collecting the solid thus formed by filtration.

In accordance with another of the process aspects of this invention, the 2-$R^4$-3-$R^1$-6-$(R)_2$-amino-5'/6'-carboxyfluorans of Formula Ia wherein Y is OH can be conveniently obtained by heating the appropriate 3-[2-hydroxy-4-$(R)_2$aminophenyl]-3-(2-$R^3$-4-$R^1$-5-$R^4$-phenyl)-5/6-carboxyphthalide in the presence of an alkali metal hydroxide or carbonate, for example, sodium hydroxide or potassium hydroxide or carbonate in a reaction medium, for example, dimethylsulfoxide at a temperature in the approximate range of 50° to 80° C.

for a period of approximately one to approximately three hours. The product is isolated by adding dilute aqueous sodium chloride to the reaction mixture followed by acidification with a dilute mineral acid, for example, hydrochloric acid the product is collected by filtration.

In accordance with a further process aspect of the invention, the 2-$R^4$-3-$R^1$-6-$(R)_2$-amino-5'/6'-$R^2O$-carbonylfluorans of Formula I wherein $R^2$ is non-tertiary $C_1$ to $C_{18}$ alkyl or benzyl are obtained by interacting a 2-$R^4$-3-$R^1$-6-$(R)_2$-amino-5'/6'-carboxyfluoran with an appropriate alkylating agent, for example, dimethyl sulfate, diethyl sulfate, ethyl iodide, n-butyl bromide, n-octyl bromide, n-hexadecyl bromide, benzyl bromide, and the like in an inert diluent, for example, N,N-dimethylformamide in the presence of an alkali metal hydroxide or carbonate, for example, sodium hydroxide, potassium hydroxide, sodium carbonate or potassium carbonate. The reaction is conveniently carried out at a temperature in the approximate range of 30°–60° C. for approximately one-half to three hours. The 2-$R^4$-3-$R^1$-6-$(R)_2$-amino-5'/6'-$R^2O$-carbonylfluoran thus obtained is isolated by slowly adding the reaction mixture to dilute aqueous sodium chloride and ammonia solution. The product which separates is then collected by filtration.

In accordance with one of the process aspects of this invention, the 2-amino-3-$R^1$-6-$(R)_2$amino-5'/6'-carboxyfluorans of Formula Ib are obtained by interacting, in a first step, in approximately equimolecular proportions of an appropriate 4/5-carboxy-2-[4-$(R)_2$amino-2-hydroxybenzoyl]benzoic acid with an appropriate 2-$R^1$-4-hydroxyacetanilide. This first step of the reaction is conveniently carried out in a dehydrating solvent, for example, 100 percent sulfuric acid at a temperature in the approximate range of 0°–80° C. for from approximately four to ten hours. The reaction mixture is then added to ice and when this addition is complete, the resulting mixture is heated to a temperature in the approximate range of 70° to 90° C. and maintained for approximately one hour. In a second step, the 2-amino-3-$R^1$-6-$(R)_2$-amino-5'/6'-carboxyfluoran can be conveniently obtained by adjusting the pH of the slurry from the first step to approximately 10.0 and heating the resulting mixture at a temperature in the approximate range of 70° to 90° C. for from approximately thirty minutes to two hours. After cooling to ambient temperature, the pH of the suspension is then adjusted to approximately 3.0 with the addition of an acid, for example, hydrochloric acid and the product is collected by filtration.

In accordance with another of the process aspects of this invention, the 2-acetamido-3-$R^1$-6-$(R)_2$amino-5'/6'-carboxyfluorans of Formula Ib are prepared by interacting in approximately equimolecular proportions of an appropriate 4/5-carboxy-2-[4-$(R)_2$amino-2-hydroxybenzoyl]benzoic acid with an appropriate 2-$R^1$-4-hydroxyacetanilide. This reaction is conveniently carried out in a dehydrating solvent, for example, 100 percent sulfuric acid at a temperature in the range of 0° to 80° C. for from approximately three to eight hours. The 2-acetamido-3-$R^1$-6-$(R)_2$amino-5'/6'-carboxyfluorans thus obtained are isolated by adding the reaction mixture to ice and collecting the solid thus formed by filtration.

In accordance with another process aspect of this invention, the 2-(1-pyrrolyl)-3-$R^1$-6-$(R)_2$amino-5'/6'-carboxyfluorans of Formula Ib are obtained by interacting the appropriate 2-amino-3-$R^1$-6-$(R)_2$amino-5'/6'-carboxyfluoran with 2,5-dialkoxytetrahydrofuran in an inert diluent, for example, ethyl alcohol in the presence of an acid, for example, hydrochloric acid. The reaction is conveniently carried out at the reflux temperature of the inert diluent for from approximately one to four hours. The 2-(1-pyrrolyl)-3-$R^1$-6-$(R)_2$amino-5'/6'-carboxyfluorans thus obtained are isolated by adding the reaction mixture to water containing an alkali, for example, ammonium hydroxide and then adjusting the pH to approximately 3.0 with an acid, for example, hydrochloric acid and collecting the solid thus formed by filtration.

In accordance with still another of the process aspects of this invention, the 2-(2,5-dimethyl-1-pyrrolyl)-3-$R^1$-6-$(R)_2$amino-5'/6'-carboxyfluorans of Formula Ib are obtained by interacting an appropriate 2-amino-3-$R^1$-6-$(R)_2$amino-5'/6'-carboxyfluoran with 2,5-hexanedione in an inert diluent, for example, ethyl alcohol in the presence of an acid, for example, hydrochloric acid. The reaction is conveniently carried out at the reflux temperature of the inert diluent and for from approximately one to approximately four hours. The 2-(2,5-dimethyl-1-pyrrolyl)-3-$R^1$-6-$(R)_2$amino-5'/6'-carboxyfluorans thus obtained are isolated by adding the reaction mixture to water and collecting the solids thus formed by filtration.

In accordance with yet another of the process aspects of this invention, the 1-$R^o$-3-$R^1$-6-$(R)_2$amino-5'/6'-carboxyfluorans of Formula Ib are obtained by interacting in approximately equimolecular proportions of an appropriate 4/5-carboxy-2-[4-$(R)_2$-amino-2-hydroxybenzoyl]benzoic acid with an appropriate 3-$R^o$-5-$R^1$-7-phenol. The reaction is conveniently carried out in a dehydrating solvent, for example, 100 percent sulfuric acid at a temperature in the range of 0° to 80° C. for from approximately three to approximately eight hours. The 1-$R^o$-3-$R^1$-6-$(R)_2$amino-5'/6'-carboxyfluorans thus obtained are isolated by adding the reaction mixture to ice water and collecting the solid thus formed by filtration.

In accordance with still yet another of the process aspects of this invention, 2-$(R^5)(R^6)$amino-3-$R^1$-6-$(R)_2$amino-5'/6'-$R^2O$-carbonylfluorans, the 2-acetamido-3-$R^1$-6-$(R)_2$amino-5'/6'-$R^2O$-carbonylfluorans, the 2-[2,5-$(R^7)_2$-1-pyrrolyl]-3-$R^1$-6-$(R)_2$amino-5'/6'-$R^2O$-carbonylfluorans and the 1-$R^o$-3-$R^1$-6-$(R)_2$amino-5'/6'-$R^2O$-carbonylfluorans of Formula Ib wherein $R^2$ is non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy are obtained by interacting a 2-amino-3-$R^1$-6-$(R)_2$amino-5'/6'-carboxyfluoran, a 2-acetamido-3-$R^1$-6-$(R)_2$amino-5'/6'-carboxyfluoran, a 2-[2,5-$(R^7)_2$-1-pyrrolyl]-3-$R^1$-6-$(R)_2$amino-5'/6'-carboxyfluoran or a 1-$R^o$-3-$R^1$-6-$(R)_2$amino-5'/6'-carboxyfluoran respectively with an appropriate alkylating agent, for example, dimethyl sulfate, diethyl sulfate, ethyl iodide, n-butyl bromide, n-hexadecyl bromide, benzyl bromide, benzyl chloride, and the like in an inert diluent, for example, N,N-dimethylformamide, acetone, isopropyl alcohol and the like in the presence of an alkali metal hydroxide or carbonate, for example, sodium hydroxide, potassium hydroxide, sodium carbonate or potassium carbonate. The reaction is conveniently carried out at a temperature in the range of 30°–60° C. for approximately one-half hour to twenty hours. The corresponding fluorans thus obtained are isolated by slowly adding the reaction mixture to dilute aqueous sodium chloride solution either with or without ammonium being present. The product which separates is then collected by filtration.

The 4/5-carboxy-2-[4-(R)$_2$amino-2-hydroxybenzoyl]-benzoic acids having the formula

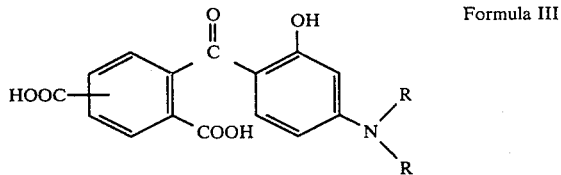

Formula III required for the preparation of the 3-[2-hydroxy-4-(R)$_2$aminophenyl]-3-2-R$^3$-4-R$^1$-5-R$^4$-phenyl)-5/6-carboxyphthalides of Formula II are generally known or if specifically new can be prepared in accordance with the procedures described for the preparation of the known compounds, for example, as disclosed in British Pat. No. 1,427,318, published Mar. 10, 1976, i.e., by interacting trimellitic anhydride with an appropriate m-(R)$_2$aminophenol in an inert diluent, for example, toluene or ethylene dichloride wherein R has the meanings given in relation to Formula I above.

It will, of course, be appreciated that the reaction of trimellitic anhydride with a m-(R)$_2$aminophenol can produce isomers or a mixture of isomers, viz. 4-carboxy-2-[4-(R)$_2$amino-2-hydroxybenzoyl]benzoic acids and 5-carboxy-2-[4-(R)$_2$amino-2-hydroxybenzoyl]benzoic acids. In the latter instance, the isomeric mixtures of the benzoic acids can be separated by conventional means such as fractional crystallization or chromatography. Alternatively, the isomeric mixtures of the 4/5-carboxy benzoic acids can be reacted with the appropriate 2-R$^1$-4-R$^3$-N-R$^4$-anilines to produce a mixture of 5- and 6-carboxyphthalides of Formula II which, if desired, can be separated or simply used as a mixture in preparing the final products of Formula I. Throughout this application where the possibility of different isomeric products being formed is present, the nomenclature 4/5, 5/6 and 5'/6' is adopted meaning the product obtained or claimed is a mixture of the isomers.

The m-(R)$_2$-aminophenols, the 2-R$^1$-4-R$^3$-N-R$^4$-anilines, 3-R$^o$-5-R$^1$-phenols, 4-hydroxyanilines and trimellitic anhydride required as starting materials in the processes of this invention belong to well known classes of compounds and are either commercially available or readily obtained by conventional procedures well known in the art.

The molecular structures of the compounds were assigned on the basis of the modes of synthesis and a study of their infrared, nuclear magnetic resonance, and mass spectra.

The following examples will further illustrate the invention without, however, limiting it thereto.

EXAMPLE 1

A. A mixture of 19.1 g (0.1 mole) of trimellitic anhydride, 16.5 g of m-diethylaminophenol (0.1 mole) and 80.0 ml of dry ethylene dichloride was heated at reflux for one hour. The reaction was then allowed to cool to room temperature and 100.0 ml of water and 22.0 ml of concentrated ammonium hydroxide were added to the reaction mixture and the ethylene dichloride layer was separated from the basic aqueous layer. The aqueous layer was extracted with 7.0 ml of petroleum ether to remove residue ethylene dichloride and then nitrogen gas was bubbled into this aqueous solution to remove residue petroleum ether. The alkaline extract was acidified with dilute hydrochloric acid to pH 4.75 and the precipitate which separated was removed by filtration. The filtrate was then adjusted to pH 3.0 and the separated solid was collected, washed with water and dried to obtain 7.7 g of 4/5-carboxy-2-(4-diethylamino-2-hydroxybenzoyl)benzoic acid (Formula III: R=CH$_2$CH$_3$), an orange solid having a melting point of 188°–190° C. A significant maximum appeared in the ultraviolet spectrum at 353 nm. The infrared spectrum and the nuclear magnetic resonance spectrum were in accord with the structure.

B. To a stirred mixture of 42.0 ml of 100 percent sulfuric acid and 10.0 ml of 18.9 percent oleum, there was added in small portions 16.0 g (0.045 mole) of 4/5-carboxy-2-(4-diethylamino-2-hydroxybenzoyl)benzoic acid prepared as described in part A above. The deep red solution was then cooled to 5° C., and 13.6 g (0.046 mole; 76.9 percent assay) of 2-methyl-N-phenyl-p-phenetidine was added. The reaction mixture was then maintained at 15°–20° C. for an additional three and a half hours. After drowning the reaction mixture in 700.0 ml of ice-water, the solid which formed was collected by filtration, washed with water and dried to obtain 28.7 g of 3-(2-hydroxy-4-diethylaminophenyl)-3-(2-ethoxy-4-methyl-5-anilinophenyl)-5/6-carboxyphthalide (Formula IIa: R=CH$_2$CH$_3$; R$^1$=CH$_3$; R$^3$=OCH$_2$CH$_3$), a purple solid which melted with decomposition at 180°–190° C. Infrared maxima appeared at 1765 cm$^{-1}$ (C=O;s) and 1715 cm$^{-1}$ (C=O;s).

C. To a solution of 32.4 g (71 percent pulp) of 3-(2-hydroxy-4-diethylaminophenyl)-3-(2-ethoxy-4-methyl-5-anilinophenyl)-5/6-carboxyphthalide, described in part B of this example, in 150.0 ml of dimethylsulfoxide, there was added 23.0 g of 50 percent aqueous sodium hydroxide solution at such a rate as to allow the reaction to exotherm to 50° C. After the addition was complete, the solution was heated to 70° C. and held there for a period of one hour and then allowed to cool to 25° C. After treatment with decolorizing charcoal, the solution was quenched with 950.0 ml of 5 percent aqueous salt solution. The alkaline solution was then acidified with dilute hydrochloric acid to pH 3.5 and the separated solid collected, washed with water and dried to obtain 13.1 g of 2-anilino-3-methyl-6-diethylamino-5'/6'-carboxyfluoran (Formula Ia: R=CH$_2$CH$_3$; R$^1$=CH$_3$; Y=OH), a black solid which melted with decomposition at 110°–115° C. Infrared maxima appeared at 1760 cm$^{-1}$ (C=O;s) and 1705 cm$^{-1}$ (C=O;s).

D. Six grams of diethyl sulfate was added to a preheated (40° C.) mixture of 10.4 g of the 2-anilino-3-methyl-6-diethylamino-5'/6'-carboxyfluoran prepared as described in part C above, 5.2 g of potassium carbonate and 50.0 ml of dimethylformamide. The reaction mixture was heated at 45° C. for a period of one-half hour. After treatment with decolorizing charcoal, the dimethylformamide filtrate was slowly added to a solution of 400.0 ml of 5 percent aqueous salt solution plus 10.0 ml of concentrated ammonium hydroxide. The solid which separated was collected by filtration, washed with water and dried to obtain 6.8 g of 2-anilino-3-methyl-6-diethylamino-5'/6'-ethoxycarbonylfluoran (Formula Ia: R=CH$_2$CH$_3$; R$^1$=CH$_3$; Y=OC$_2$H$_5$), as a light purple solid melting over the range 104°–107° C. Infrared maxima appeared at 1768 cm$^{-1}$ (C=O;s) and 1725 cm$^{-1}$ (C=O;s). A toluene solution of the product spotted on silica gel, an acidic clay or a phenoic resin developed a black-colored image.

EXAMPLE 2

Five milliliters of dimethylsulfate was added to a preheated (45° C.) mixture of 5.0 g of the 2-anilino-3-methyl-6-diethylamino-5'/6'-carboxyfluoran, prepared as described in Example 1, part C above, 5.0 g of potassium carbonate and 150.0 ml of dimethylformamide. The reaction mixture was heated at 45° C. for a period of one hour and was then poured into water and extracted with toluene. The toluene extract was washed successively with water and saturated salt solution and then evaporated to dryness. The residue was triturated with hexane and the solid separated and dried to obtain 2.4 g of 2-anilino-3-methyl-6-diethylamino-5'/6'-methoxycarbonylfluoran (Formula Ia: $R=CH_2CH_3$; $R^1=CH_3$; $Y=OCH_3$) as a light gray solid melting over the range 87°–98° C. Infrared maxima appeared at 1765 cm$^{-1}$ (C=O;s) and 1725 cm$^{-1}$ (C=O;s). A toluene solution of the product spotted on silica gel, an acidic clay or a phenolic resin developed a black-colored image.

EXAMPLE 3

Following a procedure similar to that described above in Example 2, except that α-bromotoluene was used in place of dimethylsulfate, there was obtained 2-anilino-3-methyl-6-diethylamino-5'/6'-phenylmethoxycarbonylfluoran (Formula Ia: $R=CH_2CH_3$; $R^1=CH_3$; $Y=OCH_2C_6H_5$), a light brown solid melting over the range 65°–94.5° C. Infrared maxima appeared at 1762 cm$^{-1}$ (C=O;s) and 1720 cm$^{-1}$ (C=O;s). A toluene solution of the product spotted on silica gel, an acidic clay or a phenolic resin developed a black-colored image.

EXAMPLE 4

Employing a procedure similar to that described in Example 3 but substituting n-butylbromide for α-bromotoluene, there was obtained 2-anilino-3-methyl-6-diethylamino-5'/6'-n-butoxycarbonylfluoran (Formula Ia: $R=CH_2CH_3$; $R^1=CH_3$; $Y=O$-n-$C_4H_9$), a light purple solid melting over the range 76°–83° C. Infrared maxima appeared at 1765 cm$^{-1}$ (C=O;s) and 1725 cm$^{-1}$ (C=O;s). A toluene solution of the product spotted on silica gel, an acidic clay or a phenolic resin developed a black-colored image.

EXAMPLE 5

When 1-bromohexadecane was substituted for α-bromotoluene in Example 3, there was obtained 2-anilino-3-methyl-6-diethylamino-5'/6'-n-hexadecyloxycarbonylfluoran (Formula Ia: $R=CH_2CH_3$; $R^1=CH_3$; $Y=O$-n-$C_{16}H_{33}$) as a purple oil. Analysis by mass spectrum showed m/e peaks at 744 (m+) and 700 (m+-$CO_2$). A toluene solution of the product spotted on silica gel, an acidic clay or a phenolic resin developed a black-colored image.

EXAMPLE 6

A. Employing a procedure similar to that described in part B of Example 1, 30.0 g (0.084 mole) of 4/5-carboxy-2-(4-diethylamino-2-hydroxybenzoyl)benzoic acid, prepared as described in part A of Example 1, was interacted with 23.5 g (0.11 mole) of N-phenyl-p-phenetidine to obtain 49.0 g of 3-(2-hydroxy-4-diethylaminophenyl)-3-(2-ethoxy-5-anilinophenyl)-5/6-carboxyphthalide (Formula IIa: $R=CH_2CH_3$; $R^1=H$; $R^3=OCH_2CH_3$) a purple solid which melted with decomposition at 98°–155° C. Infrared maxima appeared at 1762 cm$^{-1}$ (C=O;s) and 1732 cm$^{-1}$ (C=O;s).

B. Following a procedure similar to that described in Example 1, part C above, except that 10.0 g of 3-(2-hydroxy-4-diethylaminophenyl)-3-(2-ethoxy-5-anilinophenyl)-5/6-carboxyphthalide, prepared as described in part A of this example, was used in place of 3-(2-hydroxy-4-diethylaminophenyl)-3-(2-ethoxy-4-methyl-5-anilinophenyl)-5/6-carboxyphthalide, there was obtained 5.8 g of 2-anilino-6-diethylamino-5'/6'-carboxyfluoran (Formula Ia: $R=CH_2CH_3$; $R^1=H$; $Y=OH$), a purple solid which melted with decomposition at 135°–148° C. Infrared maxima appeared at 1756 cm$^{-1}$ (C=O;s) and 1705 cm$^{-1}$ (C=O;s).

C. Employing a procedure similar to that described in Example 2, but interacting 5.0 g of 2-anilino-6-diethylamino-5'/6'-carboxyfluoran prepared as described in Part B of this example with dimethyl sulfate, there was obtained 2.1 g of 2-anilino-6-diethylamino-5'/6'-methoxycarbonylfluoran (Formula Ia: $R=CH_2CH_3$; $R^1=H$; $Y=OCH_3$), a gray solid melting over the range 71°–76° C. Infrared maxima appeared at 1765 cm$^{-1}$ (C=O;s) and 1730 cm$^{-1}$ (C=O;s). Analysis by mass spectrum showed m/e peaks at 520 (m+), 476 (m+-$CO_2$) and 461 (m+-$COOCH_3$). A toluene solution of the product spotted on silica gel, an acidic clay or a phenolic resin developed a green-black-colored image.

EXAMPLE 7

When diethylsulfate was substituted for dimethylsulfate for interaction with 10.0 g of 2-anilino-6-diethylamino-5'/6'-carboxyfluoran according to the procedure described in part C of Example 6, there was obtained 5.1 g of 2-anilino-6-diethylamino-5'/6'-ethoxycarbonylfluoran (Formula Ia: $R=CH_2CH_3$; $R^1=H$; $Y=OCH_2CH_3$), a light grape-colored solid melting over the range 70°–85° C. Infrared maxima appeared at 1768 cm$^{-1}$ (C=O;s) and 1720 cm$^{-1}$ (C=O;s). The nuclear magnetic resonance spectrum was in agreement with the assigned structure. Analysis by mass spectrum showed m/e peaks at 534 (m+), 489 (m+-COOH) and 461 (m+-$COOC_2H_5$). A toluene solution of the product spotted on silica gel, an acidic clay or a phenolic resin developed a green-black-colored image.

EXAMPLE 8

A. Following a procedure similar to that described above in part A of Example 1 but substituting m-dimethylaminophenol for m-diethylaminophenol, there was obtained 4/5-carboxy-2-(4-dimethylamino-2-hydroxybenzoyl)benzoic acid (Formula III: $R=CH_3$), a yellow solid having a melting point of 233°–236° C. The infrared spectrum and the nuclear magnetic resonance spectrum were in accord with the structure. Analysis by mass spectrum showed m/e peaks at 329 (m+) and 284 (m+-COOH).

B. A mixture of 16.5 g (0.05 mole) of 4/5-carboxy-2-(4-dimethylamino-2-hydroxybenzoyl)benzoic acid from part A above, and concentrated sulfuric acid was interacted with N-phenyl-p-phenetidine in a manner similar to that described above in Example 6, part A to obtain 17.5 g of 3-(2-hydroxy-4-dimethylaminophenyl)-3-(2-ethoxy-5-anilinophenyl)-5/6-carboxyphthalide (Formula IIa: $R=CH_3$; $R^1=H$; $R^3=OCH_2CH_3$), a purple solid which melted with decomposition at 119°–134° C.

Infrared maxima appeared at 1770 cm$^{-1}$ (C=O;s) and 1715 cm$^{-1}$ (C=O;s).

C. Proceeding in a manner similar to part B of Example 6, but substituting 16.7 g of 3-(2-hydroxy-4-dimethylaminophenyl)-3-(2-ethoxy-5-anilinophenyl)-5/6-carboxyphthalide, prepared as described in part B above, for 3-(2-hydroxy-4-diethylaminophenyl)-3-(2-ethoxy-5-anilinophenyl)-5/6-carboxyphthalide, there was obtained 7.5 g of 2-anilino-6-dimethylamino-5'/6'-carboxyfluoran (Formula Ia: R=CH$_3$; R$^1$=H; Y=OH), a purple solid melting at 180°–183° C. Infrared maxima appeared at 1750 cm$^{-1}$ (C=O;s) and 1690 cm$^{-1}$ (C=O;s). Analysis by mass spectrum showed m/e peaks at 478 (m+) and at 433 (m+-COOH).

D. Employing a procedure similar to that described in Example 2, but interacting 5.0 g of 2-anilino-6-dimethylamino-5'/6'-carboxyfluoran, prepared as described in part C of this example, with dimethyl sulfate there was obtained 1.8 g of 2-anilino-6-dimethylamino-5'/6'-methoxycarbonylfluoran (Formula Ia: R=CH$_3$; R$^1$=H; Y=OCH$_3$), a gray solid melting over the range of 97.5°–115° C. Infrared maxima appeared at 1763 cm$^{-1}$ (C=O;s) and 1725 cm$^{-1}$ (C=O;s). Analysis by mass spectrum showed m/e peaks at 492 (m+), 448 (m+-CO$_2$) and 433 (m+-COOCH$_3$). A toluene solution of the product spotted on silica gel, an acidic clay or a phenolic resin developed a green-black-colored image.

It is contemplated that by following the procedure described in Example 1, part B above, but using in place of 4/5-carboxy-2-(4-diethylamino-2-hydroxybenzoyl)-benzoic acid and 2-methyl-N-phenyl-p-phenetidine approximately molar equivalent quantities of the appropriate 4/5-carboxy-2-[4-(R)$_2$-amino-2-hydroxybenzoyl]-benzoic acid and the appropriate 2-R$^1$-4-R$^3$-diphenylamine the following 3-[2-hydroxy-4-(R)$_2$aminophenyl]-3-(2-R$^3$-4-R$^1$-5-anilinophenyl)-5/6-carboxyphthalides of Formula IIa described in Examples 9–12 are obtained.

EXAMPLE 9

3-(2-Hydroxy-4-di-n-propylaminophenyl)-3-(2-methoxy-4-ethyl-5-anilinophenyl)-5/6-carboxyphthalide using 4/5-carboxy-2-(4-di-n-propylamino-2-hydroxybenzoyl)benzoic acid and 2-ethyl-4-methoxydiphenylamine.

EXAMPLE 10

3-(2-Hydroxy-4-di-s-butylaminophenyl)-3-(2-n-butoxy-5-anilinophenyl)-5/6-carboxyphthalide using 4/5-carboxy-2-(4-di-s-butylamino-2-hydroxybenzoyl)-benzoic acid and 4-n-butoxydiphenylamine.

EXAMPLE 11

3-(2-Hydroxy-4-di-i-propylaminophenyl)-3-(2-n-propoxy-4-n-butyl-5-anilinophenyl)-5/6-carboxyphthalide using 4/5-carboxy-2-(4-di-i-propylamino-2-hydroxybenzoyl)benzoic acid and 4-n-propoxy-2-n-butyldiphenylamine.

EXAMPLE 12

3-(2-Hydroxy-4-di-n-butylaminophenyl)-3-(2-s-butoxy-4-methyl-5-anilinophenyl)-5/6-carboxyphthalide using 4/5-carboxy-2-(4-di-n-butylamino-2-hydroxybenzoyl)benzoic acid and 4-s-butoxy-2-methyldiphenylamine.

It is contemplated that by following the procedure described in Example 1, part C above, but using in place of 3-(2-hydroxy-4-diethylaminophenyl)-3-(2-ethoxy-4-methyl-5-anilinophenyl)-5/6-carboxyphthalide and sodium hydroxide the appropriate 3-[2-hydroxy-4-(R)$_2$aminophenyl]-3-(2-R$^3$-4-R$^1$-5-anilinophenyl)-5/6-carboxyphthalide and alkali metal hydroxide or ammonium hydroxide the following 2-anilino-3-R$^1$-6-(R)$_2$amino-5'/6'-carboxyfluorans of Formula Ia wherein Y is OH described in Examples 13–16 are obtained.

EXAMPLE 13

2-Anilino-3-ethyl-6-di-n-propylamino-5'/6'-carboxyfluoran using 3-(2-hydroxy-4-di-n-propylaminophenyl)-3-(2-methoxy-4-ethyl-5-anilinophenyl)-5/6-carboxyphthalide and potassium hydroxide.

EXAMPLE 14

2-Anilino-6-di-s-butylamino-5'/6'-carboxyfluoran using 3-(2-hydroxy-4-di-s-butylaminophenyl)-3-(2-n-butoxy-5-anilinophenyl)-5/6-carboxyphthalide and lithium hydroxide.

EXAMPLE 15

2-Anilino-3-n-butyl-6-di-i-propylamino-5'/6'-carboxyfluoran using 3-(2-hydroxy-4-di-i-propylaminophenyl)-3-(2n-propoxy-4-n-butyl-5-anilinophenyl)-5/6-carboxyphthalide and ammonium hydroxide.

EXAMPLE 16

2-Anilino-3-methyl-6-di-n-butylamino-5'/6'-carboxyfluoran using 3-(2-hydroxy-4-di-n-butylaminophenyl)-3-(2-s-butoxy-4-methyl-5-anilinophenyl)-5/6-carboxyphthalide and potassium hydroxide.

It is contemplated that by following the procedure described in Example 1, part D above, but using in place of 2-anilino-3-methyl-6-diethylamino-5'/6'-carboxyfluoran and diethyl sulfate the appropriate 2-anilino-3-R$^1$-6-(R)$_2$amino-5'/6'-carboxyfluoran and the appropriate compound selected from the group consisting of dimethyl sulfate, diethyl sulfate, non-tertiary C$_1$ to C$_{18}$ alkyl halogen or benzyl halide the following 2-anilino-3-R$^1$-6-(R)$_2$amino-5'/6'-Y-carbonylfluoran of Formula Ia wherein Y represents R$^2$O in which R$^2$ is a non-tertiary C$_1$ to C$_{18}$ alkyl or benzyl described in Examples 17–20 are obtained.

EXAMPLE 17

2-Anilino-3-ethyl-6-di-n-propylamino-5'/6'-n-hexyloxy-carbonylfluoran using 2-anilino-3-ethyl-6-di-n-propylamino-5'/6'-carboxyfluoran and n-hexylbromide.

EXAMPLE 18

2-Anilino-6-di-s-butylamino-5'/6'-n-octadecyloxycarbonylfluoran using 2-anilino-6-di-s-butylamino-5'/6'-carboxyfluoran and n-octadecylbromide.

EXAMPLE 19

2-Anilino-3-n-butyl-6-di-i-propylamino-5'/6'-i-octyloxycarbonylfluoran using 2-anilino-3-n-butyl-6-di-i-propylamino-5'/6'-carboxyfluoran and i-octylbromide.

EXAMPLE 20

2-Anilino-3-methyl-6-di-n-butylamino-5'/6'-n-dodecyloxycarbonylfluoran using 2-anilino-3-methyl-6-di-n-butylamino-5'/6'-carboxyfluoran and n-dodecyliodide.

EXAMPLE 21

A. With stirring there was added in small portions 17.8 g (0.05 mole) of 4/5-carboxy-2-(4-diethylamino-2-hydroxybenzoyl)benzoic acid prepared as described in Example 1, part A above to 50.0 ml of 100 percent sulfuric acid. The deep red solution was then cooled to 5° C., and 8.2 g (0.054 mole) of 4-hydroxyacetanilide was slowly added. The reaction mixture was then maintained at ambient temperature for an additional four and one-half hours. The reaction mixture was then heated to and maintained at approximately 60° C. for an additional three hours. The reaction mixture was then poured onto crushed ice with stirring and the resultant mixture allowed to set overnight. The solid which formed was collected by filtration, washed with water and dried to obtain 7.7 g of 2-acetamido-6-diethylamino-5'/6'-carboxyfluoran (Formula Ib: $R=CH_2CH_3$; $R^o=R^1=H$; $R^{4'}=NHCOCH_3$; $Y=OH$) a dark red solid which melted at 83°–87° C. Infrared maxima appeared at 1760 cm$^{-1}$ (C=O;s) and 1700 (C=O;w).

B. Slowly 4.6 g (0.03 mole) of diethyl sulfate was added to a preheated (40°–50° C.) mixture of 7.1 g (0.015 mole) of 2-acetamido-6-diethylamino-5'/6'-carboxyfluoran prepared as described in part A above, 5.6 g of potassium carbonate and 30.0 ml of dimethylformamide. The reaction mixture was heated at 40°–45° C. for a period of four hours. The reaction mixture was cooled to 30° C., the solid was collected by filtration, washed with water and dried to obtain 0.15 g. The filtrate was slowly added to a solution of 400.0 ml of 5 percent aqueous sodium chloride solution plus a few drops of concentrated ammonium hydroxide. The solid which separated was collected by filtration, washed with water and dried to obtain 4.5 g of 2-acetamido-6-diethylamino-5'/6'-ethoxycarbonylfluoran (Formula Ib: $R^o=R^1=H$; $R=CH_2CH_3$; $R^{4'}=NHCOCH_3$; $Y=OC_2H_5$), as a pink solid melting at 150°–153° C. Infrared maxima appeared at 1770 cm$^{-1}$ (C=O;s) and 1725 cm$^{-1}$ (C=O;s). A toluene solution of the product spotted on silica gel, an acidic clay or a phenolic resin developed a red-colored image.

EXAMPLE 22

A. To 280.0 ml of 100 percent sulfuric acid, there was added with stirring in small portions 106.8 g (0.30 mole) of 4/5-carboxy-2-(4-diethylamino-2-hydroxybenzoyl)benzoic acid prepared as described in Example 1, part A above. The deep red solution was cooled to 25° C. and slowly 51.4 g (0.34 mole) of 4-hydroxyacetanilide was added. The reaction mixture was then maintained at 80° C. for five hours. After drowning the reaction mixture on crushed ice, the resulting mixture was allowed to set overnight. In the morning, the mixture was heated at 80° C. for one hour, cooled to 25° C. and the pH adjusted to 10.2 by the addition of 634.0 ml of 50 percent aqueous sodium hydroxide. The resultant mixture was heated at 80° C. for approximately thirty minutes and cooled to 25° C. The volume of the mixture was adjusted to 1500.0 ml by adding water and the pH was adjusted to 3.1 with the addition of 75.0 ml of concentrated hydrochloric acid. The solid was collected by filtration, washed with water which had been adjusted to pH 3.0 with hydrochloric acid and dried to obtain 135.5 g of 2-amino-6-diethylamino-5'/6'-carboxyfluoran (Formula Ib: $R^o=R^1=H$; $R^{4'}=NH_2$; $R=CH_2CH_3$; $Y=OH$), a solid which melted over the range 193.1–232.2° C. Infrared maxima appeared at 1760 cm$^{-1}$ (C=O;s) and 1720 cm$^{-1}$ (C=O;s).

B. To a mixture of 100.0 ml of 85 percent aqueous dimethylformamide, 10.8 g (0.025 mole) of 2-amino-6-diethylamino-5'/6'-carboxyfluoran from part A above and 27.6 g of potassium carbonate there was slowly added over a period of fifteen minutes at 40° C. 31.0 g (0.20 mole) of diethyl sulfate. The resulting mixture was heated at 40°–45° C. for eighteen hours and 30.0 ml of dimethylformamide and 5.9 g (0.038 mole) of diethyl sulfate was added. After heating at 50° C. an additional sixteen hours, the reaction mixture was poured slowly into 700.0 ml of water. The solid which formed was collected by filtration, washed with water and dried to obtain 11.0 g of a mixture of 2,6-bis(diethylamino)-5'/6'-ethoxycarbonylfluoran (major component) (Formula Ib: $R^o=R^1=H$; $R=CH_2CH_3$; $R^{4'}=N(C_2H_5)_2$; $Y=OC_2H_5$), 2-ethylamino-6-diethylamino-5'/6'-ethoxycarbonylfluoran (Formula Ib: $R^o=R^1=H$; $R=CH_2CH_3$; $R^{4'}=NHC_2H_5$; $Y=OC_2H_5$), a pale grape-colored solid which melted over the range 62.0°–90.0° C. Infrared maxima appeared at 1770 cm$^{-1}$ (C=O;s) and 1728 cm$^{-1}$ (C=O;s). A toluene solution of the product spotted on silica gel, an acidic clay or a phenolic resin developed a green-colored image.

C. With stirring 10.8 g (0.02 mole) of 2-amino-6-diethylamino-5'/6'-carboxyfluoran from part A above was dissolved in 175.0 ml of acetone and 27.6 g of potassium carbonate was added. Slowly 17.1 g (0.13 mole) of benzyl chloride was added and the resulting mixture heated at reflux for approximately sixteen hours. After cooling to room temperature, the reaction mixture was slowly poured into 600.0 ml of water and a gummy oil separated from the water layer. The water-oil mixture was extracted with 500.0 ml of toluene and the toluene layer separated. The toluene layer was washed with water and saturated aqueous sodium chloride solution, then treated with 5.0 g of decolorizing charcoal, filtered and evaporated to dryness. The residue was extracted three times each with 150.0 ml of hexane, decanting the hexane extract. The resulting residue was dried to obtain 15.3 g of 2-dibenzylamino-6-diethylamino-5'/6'-phenylmethoxycarbonylfluoran (Formula Ib: $R^o=R^1=H$; $R=CH_2CH_3$; $R^{4'}=N(CH_2C_6H_5)_2$; $Y=OCH_2-C_6H_5$), as an oil. Infrared maxima appeared at 1768 cm$^{-1}$ (C=O;s) and 1725 cm$^{-1}$ (C=O;s). A toluene solution of the product spotted on silica gel, an acidic clay or a phenolic resin developed a green-colored image.

D. A mixture of: 22.0 g (0.05 mole) of 2-amino-6-diethylamino-5'/6'-carboxyfluoran from part A above, 42.0 g of potassium carbonate, 33.0 g (0.26 mole) of benzyl chloride and 300.0 ml of isopropyl alcohol was heated at reflux for approximately 23 hours. After cooling to ambient temperature, the reaction mixture was slowly poured with stirring into 900.0 ml of water and 700.0 ml of toluene was added. The toluene layer was separated, washed with water and saturated aqueous sodium chloride solution. The resulting toluene layer was then heated under reduced pressure to remove the toluene, unreacted benzyl chloride and the byproduct benzyl alcohol to obtain 27.0 g of 2-dibenzylamino-6-diethylamino-5'/6'-i-propoxycarbonylfluoran (Formula Ib: $R^o=R^1=H$; $R=CH_2CH_3$; $R^{4'}=N(CH_2C_6H_5)_2$; $Y=O-i-C_3H_7$), a green oil. Infrared maxima appeared at 1760 cm$^{-1}$ (C=O;s) and 1720 cm$^{-1}$ (C=O;s). The nuclear magnetic resonance spectrum was consistent with the assigned structure. A toluene solution of the product spotted on silica gel; an acidic clay or a phenolic resin developed a green-colored image.

EXAMPLE 23

A. With stirring a mixture of 13.1 g (0.03 mole) of 2-amino-6-diethylamino-5′/6′-carboxyfluoran prepared as described in Example 22, part A above, 90.0 ml of ethyl alcohol, 9.0 g (0.068 mole) of 2,5-dimethoxytetrahydrofuran and 10 drops of concentrated hydrochloric acid were heated at reflux for approximately three hours. After cooling to room temperature, the reaction solution was poured with stirring into 1500.0 ml of 5 percent aqueous ammonium hydroxide. The resulting mixture was adjusted to pH 2.8 with concentrated hydrochloric acid, a small amount of sodium chloride was added and the mixture allowed to set overnight. The solid which formed was collected by filtration, washed with water and dried to obtain 11.3 g of 2-(1-pyrrolyl)-6-diethylamino-5′/6′-carboxyfluoran (Formula Ib: $R^o=R^1=H$; $R=CH_2CH_3$; $R^{4'}=1$-pyrrolyl; $Y=OH$), as a red solid which decomposed at 220° C. Infrared maxima appeared at 1760 cm$^{-1}$ (C=O;s) and 1710 cm$^{-1}$ (C=O;s). The nuclear magnetic resonance spectrum was consistent with the assigned structure.

B. Proceeding in a manner similar to that described in Example 21 part B above, 4.8 g (0.01 mole) of 2-(1-pyrrolyl)-6-diethylamino-5′/6′-carboxyfluoran was interacted with 3.1 g (0.02 mole) of diethyl sulfate in 25.0 ml of dimethylformamide and 2.8 g of potassium carbonate to obtain 4.3 g of 2-(1-pyrrolyl)-6-diethylamino-5′/6′-ethoxycarbonylfluoran (Formula Ib: $R^o=R^1=H$; $R=CH_2CH_3$; $R^{4'}=1$-pyrrolyl; $Y=OC_2H_5$), a pink solid which melted over the range 109°–128° C. Infrared maxima appeared at 1770 cm$^{-1}$ (C=O;s) and 1722 cm$^{-1}$ (C=O;s). The nuclear magnetic resonance spectrum was concordant with the assigned structure. A toluene solution of the product spotted on silica gel, an acidic clay or a phenolic resin developed a red-colored image.

C. In a manner similar to that described in Example 21, part B above, 4.8 g (0.01 mole) of 2-(1-pyrrolyl)-6-diethylamino-5′/6′-carboxyfluoran as prepared in part A directly above was interacted with 2.6 g (0.015 mole) of benzyl bromide in 25.0 ml of dimethylformamide and 2.8 g of potassium carbonate to obtain 5.5 g of 2-(1-pyrrolyl)-6-diethylamino-5′/6′-phenylmethoxycarbonylfluoran (Formula Ib: $R^o=R^1=R^7=H$; $R=CH_2CH_3$; $R^{4'}=1$-pyrrolyl; $Y=OCH_2C_6H_5$), as a pink solid which melted over the range 94°–112° C. Infrared maxima appeared at 1769 cm$^{-1}$ (C=O;s) and 1722 cm$^{-1}$ (C=O;s). The nuclear magnetic resonance spectrum was consistent with the assigned structure. A toluene solution of the product spotted on silica gel, an acidic clay or a phenolic resin developed a red-colored image.

EXAMPLE 24

A. A mixture of 13.1 g (0.03 mole) of 2-amino-6-diethylamino-5′/6′-carboxyfluoran prepared as described in Example 22, part A above, 90.0 ml of ethyl alcohol, 3.8 g of hexane-2,5-dione, and five drops of concentrated hydrochloric acid was maintained at reflux temperature for three hours. The reaction mixture was cooled to ambient temperature, poured onto one liter of water and the solid which formed was collected by filtration, washed with water and dried to obtain 13.0 g of 2-(2,5-dimethyl-1-pyrrolyl)-6-diethylamino-5′/6′-carboxyfluoran (Formula Ib: $R^o=R^1=H$; $R=CH_2CH_3$; $R^{4'}=2,5$-dimethyl-1-pyrrolyl; $Y=OH$), as a pink solid which decomposed at 200° C. Infrared maximum appeared at 1770 cm$^{-1}$ (C=O;s) and 1710 cm$^{-1}$ (C=O;s). The nuclear resonance spectrum was consistent with the assigned structure.

B. In a manner similar to that described in Example 21, part B above, 5.1 g (0.01 mole) of 2-(2,5-dimethyl-1-pyrrolyl)-6-diethylamino-5′/6′-carboxyfluoran prepared as described in part A directly above, was interacted with 2.3 g (0.015 mole) of diethyl sulfate in 35.0 ml of dimethylformamide and 2.8 g of potassium carbonate to obtain 4.5 g of 2-(2,5-dimethyl-1-pyrrolyl)-6-diethylamino-5′/6′-ethoxycarbonylfluoran (Formula Ib: $R^o=R^1=H$; $R=CH_2CH_3$; $R^{4'}=2,5$-dimethyl-1-pyrrolyl; $Y=OC_2H_5$), as a pink-colored solid which melted at 113°–123° C. Infrared maxima appeared at 1770 cm$^{-1}$ (C=O;s) and 1722 cm$^{-1}$ (C=O;s). The nuclear magnetic resonance spectrum was concordant with the assigned structure. A toluene solution of the product spotted on silica gel, an acidic clay or a phenolic resin developed a red-colored image.

C. In a procedure similar to that described in Example 21, part B above, 5.1 g (0.01 mole) of 2-(2,5-dimethyl-1-pyrrolyl)-6-diethylamino-5′/6′-carboxyfluoran was interacted with 2.1 g (0.015 mole) of n-butylbromide in 35.0 ml of dimethylformamide and 2.8 g of potassium carbonate to obtain 3.0 g of 2-(2,5-dimethyl-1-pyrrolyl)-6-diethylamino-5′/6′-n-butoxycarbonylfluoran (Formula Ib: $R^o=R^1=H$; $R=CH_2CH_3$; $R^{4'}=2,5$-dimethyl-1-pyrrolyl; $Y=OC_4H_9$), as a pink solid which melted at 95°–110° C. Infrared maxima appeared at 1770 cm$^{-1}$ (C=O;s) and 1720 cm$^{-1}$ (C=O;s). The nuclear magnetic resonance spectrum was consistent with the assigned structure. A toluene solution of the product spotted on silica gel, an acidic clay or a phenolic resin developed a red-colored image.

EXAMPLE 25

A. To 60.0 ml of 100 percent sulfuric acid, there was slowly added with stirring 21.2 g (0.06 mole) of 4/5-carboxy-2-(4-diethylamino-2-hydroxybenzoyl)benzoic acid, prepared as described in Example 1, part A above. After cooling the resulting mixture to approximately 5° C., 7.7 g (0.063 mole) of 3,5-dimethylphenol was added and the temperature was allowed to rise to 25° C. After stirring three and one-half hours at 25° C., the reaction mixture was heated at 70° C. for approximately ninety minutes, cooled to ambient temperature and allowed to set overnight. The resulting red solution was slowly poured into water and ice with stirring. The solid which formed was collected by filtration, washed with water and dried to obtain 39.0 g of 1,3-dimethyl-6-diethylamino-5′/6′-carboxyfluoran (Formula Ib: $R^o=R^1=CH_3$; $R=CH_2CH_3$; $R^{4'}=H$; $Y=OH$) as a red solid which melted over the range 234°–250° C. The nuclear magnetic resonance spectrum was in accord with the assigned structure.

B. Proceeding in a manner similar to that described in Example 21, part B above, 4.4 g (0.01 mole) of 1,3-dimethyl-6-diethylamino-5′/6′-carboxyfluoran prepared as described in part A directly above was interacted with 3.1 g (0.02 mole) of diethyl sulfate in 25.0 ml of dimethylformamide and 2.8 g of potassium carbonate to obtain 1.0 g of 1,3-dimethyl-6-diethylamino-5′/6′-ethoxycarbonylfluoran (Formula Ib: $R^o=R^1=CH_3$; $R=CH_2CH_3$; $R^{4'}=H$; $Y=OC_2H_5$) as a red solid which softened at 102° C. and melted at 133°–138° C. Infrared maxima appeared at 1770 cm$^{-1}$ (C=O;s) and 1730 cm$^{-1}$ (C=O;s). The nuclear magnetic resonance spectrum was consistent with the assigned structure. A toluene solution of the product spotted on silica gel, an acidic clay or a phenolic resin developed an orange-colored image.

C. In a manner similar to Example 21, part B above, 6.6 g (0.015 mole) of 1,3-dimethyl-6-diethylamino-5'/6'-carboxyfluoran was interacted with 3.8 g of dimethyl sulfate in 25.0 ml of dimethylformamide and 4.1 g of potassium carbonate to obtain 0.6 g of 1,3-dimethyl-6-diethylamino-5'/6'-methoxycarbonylfluoran (Formula Ib: $R^o=R^3=CH_3$; $R=CH_2CH_3$; $R^{4'}=H$; $Y=OCH_3$) as a pink solid which melted at 132°–134° C. Infrared maxima appeared at 1770 cm$^{-1}$ (C=O;s) and 1730 cm$^{-1}$ (C=O;s). The nuclear magnetic resonance spectrum was concordant with the assigned structure. A toluene solution of the product spotted on silica gel, an acidic clay or a phenolic resin developed a red-orange-colored image.

EXAMPLE 26

A. To 100.0 ml of 100 percent sulfuric acid and 10.0 ml of 28.7 percent oleum, there was added slowly with stirring maintaining a temperature below 40° C. 36.0 g (0.1 mole) 4/5-carboxy-2-(4-diethylamino-2-hydroxybenzoyl)benzoic acid, prepared as described in Example 1, part A above. After cooling the resulting mixture to approximately 10° C., 25.0 g (0.104 mole) of 1-N-benzylamino-2-methyl-4-ethoxybenzene was added maintaining a temperature in the range of 10° to 15° C. The resulting reaction mixture was stirred approximately twenty-two hours at 25° to 30° C. The resulting solution was added dropwise to a mixture of 1200.0 g of ice and 24.0 g of sodium chloride with stirring. The resulting tar-like material was collected by filtration and resuspended in a mixture of 1900.0 ml of ice and water. After approximately two hours of stirring a deep blue solid was collected by filtration, washed twice with 800.0 ml of water per wash and dried on the filter overnight to obtain 35.6 g of 3-(2-ethoxy-4-methyl-5-benzylaminophenyl)-3-(2-hydroxy-4-diethylaminophenyl)-5/6-carboxyphthalide (Formula IIb: $R=CH_2CH_3$; $R^1=CH_3$; $R^3=OCH_2CH_3$; $R^{4'}=NHCH_2C_6H_5$) a deep blue solid having a melting point of 187°–190° C. An infrared maximum appeared at 1700 cm$^{-1}$ (C=O;s).

B. To a solution of 150.0 ml of water and 20.0 g of potassium carbonate at approximately 30° C., there was added slowly with stirring 29.0 g of 3-(2-ethoxy-4-methyl-5-benzylaminophenyl)-3-(2-hydroxy-4-diethylaminophenyl)-5/6-carboxyphthalide, described in part A of this example. The pH of the resulting mixture was adjusted to 8.9 with the addition of a small amount of hydrochloric acid. The reaction mixture was heated to approximately 90° C. and held there for a period of two to three hours. After cooling to ambient temperature, the reaction mixture was slowly poured with stirring onto approximately 800.0 g of ice and the pH of the resultant mixture was adjusted to 3.0 using concentrated hydrochloric acid. The resulting solid was collected by filtration, washed twice, each with 1000.0 ml of water and allowed to dry on the filter to obtain 22.0 g of 2-benzylamino-3-methyl-6-diethylamino-5'/6'-carboxyfluoran (Formula Ib: $R=CH_2CH_3$; $R^1=CH_3$; $R^o=H$; $R^{4'}=NHCH_2C_6H_5$; $Y=OH$), a dark blue-black solid which melted at 190° to 191° C. An infrared maximum appeared at 1700 cm$^{-1}$ (C=O;s).

C. A solution of 13.4 g of 2-benzylamino-2-methyl-6-diethylamino-5'/6'-carboxyfluoran, described in part B above, 100.0 ml of N,N-dimethylformamide and 7.5 g of potassium carbonate was heated to approximately 50° C. and 4.0 g of diethylsulfate was added. The reaction mixture was maintained at a temperature in the range of 50° to 55° C. for approximately one hour and an additional 2.0 g of diethylsulfate was added. A temperature in the range of 50° to 55° C. was maintained for an additional hour. The hot reaction mixture was filtered to remove traces of insolubles and the filter cake was washed twice, each wash consisting of 20.0 ml of N,N-dimethylformamide. The combined filtrate and wash was added dropwise with stirring to a mixture of 1000.0 ml of water, 5.0 ml of concentrated ammonium hydroxide and 20.0 g of sodium chloride. The solid that formed was collected by filtration and washed five times, each with 100.0 ml of water. The water-wet filter cake was dissolved in 300.0 ml of acetone and the resulting solution stirred with 10.0 g of decolorizing carbon and filtered to remove the carbon. The filtrate was added slowly to 2000.0 ml of one percent aqueous sodium chloride solution with stirring. The solid was collected by filtration and washed five times, each with 150.0 ml of water and dried to obtain 9.5 g of 2-benzylamino-3-methyl-6-diethylamino-5'/6'-ethoxycarbonylfluoran (Formula Ib: $R=CH_2CH_3$; $R^o=H$; $R^1=CH_3$; $R^{4'}=NHCH_2C_6H_5$; $Y=OCH_2CH_3$) a grape solid which melted at 72° to 73° C. Infrared maxima appeared at 1760 cm$^{-1}$ (C=O;s) and 1720 cm$^{-1}$ (C=O;s). The nuclear magnetic resonance spectrum was consistent with the assigned structure. A toluene solution of the product spotted on silica gel, an acidic clay or a phenolic resin developed a blue-black-colored image.

It is contemplated that by following the procedure described in Example 21, part A above, but using in place of 4-hydroxyacetanilide the appropriate 4-hydroxy-2-$R^1$-acylanilide and the procedure described in Example 25, part A above, but using in place of 3,5-dimethylphenol the appropriate 3-$R^o$-5-$R^1$-phenol interacting in both instances with a 4/5-carboxy-2-[4-(R)$_2$amino-2-hydroxybenzoyl]benzoic acid in place of 4/5-carboxy-2-(4-diethylamino-2-hydroxybenzoyl)benzoic acid the following 1-$R^o$-2-$R^{4'}$-3-$R^1$-6-(R)$_2$-amino-5'/6'-Y-carboxyfluorans of Formula Ib wherein Y is OH described in Examples 27–44 of the following table are obtained.

TABLE I

| Example No. | R | $R^o$ | $R^1$ | $R^{4'}$ |
|---|---|---|---|---|
| 27 | n-C$_3$H$_7$ | H | H | NHCOC$_2$H$_5$ |
| 28 | s-C$_4$H$_9$ | H | CH$_3$ | NH$_2$ |
| 29 | i-C$_3$H$_7$ | CH$_3$ | CH$_3$ | H |
| 30 | n-C$_4$H$_9$ | H | H | NHCOC$_3$H$_7$ |
| 31 | CH$_3$ | H | C$_2$H$_5$ | H |
| 32 | CH$_3$ | CH$_3$ | CH$_3$ | H |
| 33 | n-C$_3$H$_7$ | H | CH$_3$ | NHCOC$_4$H$_9$ |
| 34 | n-C$_4$H$_9$ | H | C$_2$H$_5$ | NH$_2$ |
| 35 | i-C$_3$H$_7$ | H | n-C$_4$H$_9$ | NH$_2$ |
| 36 | CH$_3$ | H | H | NH$_2$ |
| 37 | CH$_3$ | H | CH$_3$ | NH$_2$ |
| 38 | i-C$_3$H$_7$ | H | H | NH$_2$ |
| 39 | n-C$_4$H$_9$ | C$_2$H$_5$ | H | H |
| 40 | n-C$_3$H$_7$ | CH$_3$ | CH$_3$ | H |
| 41 | s-C$_4$H$_9$ | H | CH$_3$ | H |
| 42 | C$_2$H$_5$ | H | CH$_3$ | NH$_2$ |
| 43 | n-C$_4$H$_9$ | H | CH$_3$ | NH$_2$ |
| 44 | n-C$_3$H$_7$ | H | H | NH$_2$ |

It is contemplated that by following the procedure described in Example 23, part A above or in Example 24, part A above, but using the appropriate 2-amino-3-$R^1$-6-(R)$_2$amino-5'/6'-carboxyfluoran and the appropriate 2,5-alkoxytetrahydrofuran or the appropriate 2,5-hexanedione the following 2-[2,5-($R^7$)$_2$-1-pyrrolyl]-3-$R^1$-6-(R)$_2$amino-5'/6'-Y-carboxyfluorans of Formula Ib wherein $R^1$ represents hydrogen or $C_1$ to $C_4$ alkyl, R represents $C_1$ to $C_4$ alkyl and Y is OH described in Examples 45 to 54 of the following table are obtained.

TABLE II

| Example No. | R | $R^1$ | $R^7$ |
|---|---|---|---|
| 45 | $CH_3$ | H | $CH_3$ |
| 46 | n-$C_4H_9$ | $CH_3$ | H |
| 47 | $C_2H_5$ | H | $CH_3$ |
| 48 | i-$C_3H_7$ | $C_2H_5$ | $CH_3$ |
| 49 | n-$C_3H_7$ | $CH_3$ | H |
| 50 | s-$C_4H_9$ | H | $CH_3$ |
| 51 | $CH_3$ | $C_3H_7$ | H |
| 52 | i-$C_3H_7$ | H | H |
| 53 | n-$C_4H_9$ | $CH_3$ | $CH_3$ |
| 54 | s-$C_4H_9$ | $CH_3$ | H |

It is contemplated that by following the procedure described in Example 22, part B above, but using in place of 2-amino-6-diethylamino-5'/6'-carboxyfluoran and diethyl sulfate the appropriate 2-amino-3-$R^1$-6-(R)$_2$amino-5'/6'-carboxyfluoran and the appropriate compound selected from the group consisting of dimethyl sulfate, diethyl sulfate, non-tertiary $C_1$ to $C_{18}$ alkyl halogen, benzyl halide or benzyl halide substituted in the phenyl ring by nitro, halo, $C_1$ to $C_4$ alkyl or $C_1$ to $C_4$ alkoxy the following 2-$R^{4'}$-3-$R^1$-6-(R)$_2$amino-5'/6'-Y-carbonylfluoran of Formula Ib wherein $R^{4'}$ represents -N($R^5$)($R^6$) and Y represents $R^2O$ in which $R^2$, $R^5$ and $R^6$ each are a non-tertiary $C_1$ to $C_{18}$ alkyl, benzyl or benzyl substituted by a nitro, halo, $C_1$ to $C_4$ alkyl or $C_1$ to $C_4$ alkoxy described in Examples 55 to 70 of the following table.

TABLE III

| Example No. | R | $R^o$ | $R^1$ | $R^4$ | Y |
|---|---|---|---|---|---|
| 55 | $CH_3$ | H | $CH_3$ | N($C_2H_5$)$_2$ | $C_2H_5O$ |
| 56 | i-$C_3H_7$ | H | H | N(4-$CH_3C_6H_4CH_2$)$_2$ | 4-$CH_3C_6H_4CH_2O$ |
| 57 | $C_2H_5$ | H | H | N(4-$ClC_6H_4CH_2$)$_2$ | 4-$ClC_6H_4CH_2O$ |
| 58 | n-$C_4H_9$ | $C_2H_5$ | H | H | $CH_3O$ |
| 59 | $CH_3$ | H | H | N(n-$C_{12}H_{25}$)$_2$ | n-$C_{12}H_{25}O$ |
| 60 | n-$C_3H_7$ | $CH_3$ | $CH_3$ | H | n-$C_{16}H_{33}O$ |
| 61 | $C_2H_5$ | H | H | N(4-$C_2H_5C_6H_4CH_2$)$_2$ | 4-$C_2H_5C_6H_4CH_2O$ |
| 62 | s-$C_4H_9$ | H | $CH_3$ | H | 4-$NO_2C_6H_4CH_2O$ |
| 63 | $CH_3$ | H | $CH_3$ | N(i-$C_8H_{17}$)$_2$ | i-$C_8H_{17}O$ |
| 64 | i-$C_3H_7$ | H | H | 1-pyrrolyl | 2,4-(Cl)$_2C_6H_3CH_2O$ |
| 65 | $C_2H_5$ | H | $CH_3$ | N[3,4-(Cl$_2$)$C_6H_3CH_2$]$_2$ | 3,4-(Cl)$_2C_6H_3CH_2O$ |
| 66 | n-$C_4H_9$ | H | $CH_3$ | 2,5-($CH_3$)$_2$—1-pyrrolyl | n-$C_8H_{17}O$ |
| 67 | $CH_3$ | H | $C_2H_5$ | H | n-$C_{18}H_{37}O$ |
| 68 | n-$C_3H_7$ | H | H | N(2-$ClC_6H_4CH_2$)$_2$ | 2-$ClC_6H_4CH_2O$ |
| 69 | $C_2H_5$ | H | $CH_3$ | N($C_6H_5CH_2$)$_2$ | $C_6H_5CH_2O$ |
| 70 | s-$C_4H_9$ | H | $CH_3$ | 1-pyrrolyl | n-$C_8H_{17}O$ |

EXAMPLE 71

The use of the fluoran compounds of Formula I and described in Examples 1 through 70 as color forming components in pressure-sensitive microencapsulated copying system is illustrated with reference to the product of Example 8D.

A. A mixture of 196.0 ml of distilled water and 15.0 g of pigskin gelatin was stirred at approximately 50° C. for approximately 45 minutes. There was then added to the mixture a warmed (approximately 50° C.) solution of 49.0 g of alkylated biphenyls and 1.0 g of 2-anilino-6-dimethylamino-5'/6'-methoxycarbonylfluoran prepared as described above in Example 8D. The resulting solution was stirred for approximately fifteen minutes. A second solution of 81.0 ml of distilled water and 5.0 g of carboxymethylcellulose was then prepared and warmed to approximately 50° C. for approximately one hour.

B. The two solutions, the first containing water, gelatin, alkylated biphenyls and the product, and the second containing water with carboxymethylcellulose were mixed by means of an Eppenbach Homo-Mixer (Gifford-Wood Co., Hudson, N.Y.). The pH was adjusted to 6.5 by the addition of approximately 0.7 ml of 20 percent aqueous sodium hydroxide. To the resultant mixture was added over a period of two to three minutes 650.0 ml of distilled water which had been heated to 50° C. With the stirrer running at an applied voltage of between 35 to 40 volts there was slowly added sufficient ten percent aqueous acetic acid to set the pH at 4.5, this being the point where coacervation was initialed. Four drops of 2-ethylhexanol were added to suppress foaming. After approximately twenty minutes an external ice-water bath was placed around the reactor containing the suspension. Cooling was continued and at approximately 15° C., 10.0 ml of glutaraldehyde was added over a period of five minutes. When the internal temperature reached 10° C., the Eppenbach Homo-Mixer was replaced with a conventional blade type laboratory agitator and the thus prepared suspension of microcapsules was stirred an additional three hours during which period the temperature was allowed to warm to room temperature.

C. The microcapsule suspension prepared as described in part B above was coated on paper sheets to a thickness of approximately 0.0015 inch and the coated paper aid dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep green-colored image promptly formed.

When evaluated in a duplicating system prepared and tested as described above, the product of Example 2, 2-anilino-3-methyl-6-diethylamino-5'/6'-methoxycarbonylfluoran, produced a black-colored developed image; the product of Example 22, part C, 2-dibenzylamino-6-diethylamino-5'/6'i-propoxycarbonylfluoran, produced a green-colored image; and the product of Example 26, part C, 2-benzylamino-3-methyl-6-diethylamino-5'/6'-ethoxycarbonylfluoran, produced a green-colored image.

EXAMPLE 72

The utility of the fluorans of Formula I and the phthalides of Formula II whose preparations are described in the foregoing examples as color forming components in thermal marking systems is illustrated by the incorporation and testing of the compounds of Example 6C and of Example 1B, respectively, in a thermal sensitive marking paper. The test paper was prepared by a procedure similar to that described in U.S. Pat. No. 3,539,375.

A. A mixture of 2.0 g of 2-anilino-6-diethylamino-5'/6'-methoxycarbonylfluoran, 8.6 g of a ten percent aqueous solution of polyvinyl alcohol (approximately 99 percent hydrolyzed), 3.7 g of water and 31.6 g of 1/16 inch diameter zirconium grinding beads were charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from A and 47.9 g of the slurry from B. The mixture was then uniformly coated on sheets of paper at thicknesses of approximately 0.003 inch and the coated sheets air-dried. The coated paper was tested by tracing a design on the coated side of the paper placed on a smooth flat surface with a stylus heated to approximately 125° C. A deep green-black-colored image corresponding to the traced design promptly developed. When evaluated in thermal marking paper prepared and tested as described above the product of Example 1, part B above, 3-(2-hydroxy-4-diethylaminophenyl)-3-(2-ethoxy-4-methyl-5-anilinophenyl)-5/6-carboxyphthalide, produced a brown-black-colored image; and the product of Example 26, part C above, 2-benzylamino-3-methyl-6-diethylamino-5'/6'-ethoxycarbonylfluoran produced a dark green-colored image.

What is claimed is:

1. A 3-[2-hydroxy-4-(R)$_2$aminophenyl]-3-(2-R$^3$-4-R$^1$-5-anilinophenyl)-5/6-carboxyphthalide of the formula

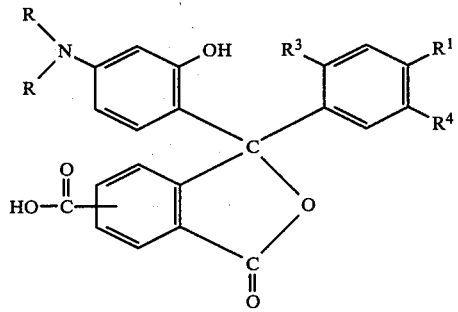

wherein:
R represents a non-tertiary $C_1$ to $C_4$ alkyl;
R$^1$ represents hydrogen or a non-tertiary $C_1$ to $C_4$ alkyl;
R$^3$ represents a non-tertiary $C_1$ to $C_4$ alkoxy;
R$^4$ represents -N(R$^5$)(R$^6$) in which
R$^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy, and
R$^6$ represents hydrogen, phenyl, non-tertiary $C_1$ to $C_{18}$ alkyl, benzyl, benzyl substituted by halo, nitro, non-tertiary $C_1$ to $C_4$ alkyl or non-tertiary $C_1$ to $C_4$ alkoxy or lower alkanoyl.

2. A 3-[2-hydroxy-4-(R)$_2$-aminophenyl]-3-(2-R$^3$-4-R$^1$-5-anilinophenyl)-5/6-carboxyphthalide of the formula

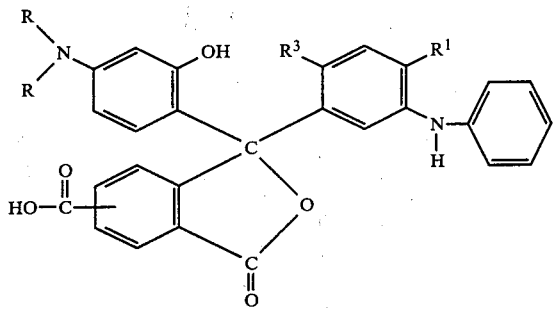

wherein:
R represents a non-tertiary $C_1$ to $C_4$ alkyl;
R$^1$ represents hydrogen or a non-tertiary $C_1$ to $C_4$ alkyl; and
R$^3$ represents a non-tertiary $C_1$ to $C_4$ alkoxy.

3. 3-(2-Hydroxy-4-diethylaminophenyl)-3-(2-ethoxy-4-methyl-5-anilinophenyl)-5/6-carboxyphthalide according to claim 2.

4. 3-(2-Hydroxy-4-dimethylaminophenyl)-3-(2-ethoxy-5-anilinophenyl)-5/6-carboxyphthalide according to claim 2.

5. 3-(2-Hydroxy-4-diethylaminophenyl)-3-(2-ethoxy-5-anilinophenyl)-5/6-carboxyphthalide according to claim 2.

6. A 3-[2-hydroxy-4-(R)$_2$-aminophenyl]-3-(2-R$^3$-4-R$^1$-5-R$^4$'-phenyl)-5/6-carboxyphthalide of the formula

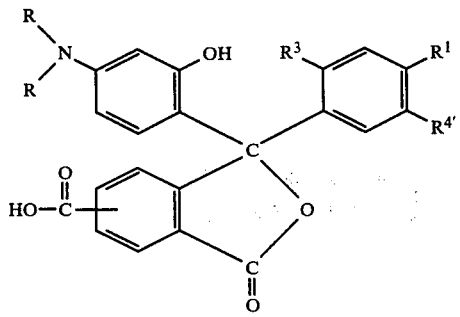

wherein:

R represents a non-tertiary $C_1$ to $C_4$ alkyl;
$R^1$ represents hydrogen or a non-tertiary $C_1$ to $C_4$ alkyl;
$R^3$ a non-tertiary $C_1$ to $C_4$ alkoxy; and
$R^{4'}$ represents $-N(R^5)(R^{6'})$ in which
$R^5$ represents hydrogen, non-tertiary $C_1$ to $C_{18}$ alkyl, benzyl or benzyl substituted by halo, nitro, non-tertiary $C_1$ to $C_4$ alkyl or non-tertiary $C_1$ to $C_4$ alkoxy, and
$R^{6'}$ represents hydrogen, non-tertiary $C_1$ to $C_{18}$ alkyl, benzyl, benzyl substituted by halo, nitro, non-tertiary $C_1$ to $C_4$ alkyl or non-tertiary $C_1$ to $C_4$ alkoxy or lower alkanoyl.

7. 3-(2-Hydroxy-4-diethylaminophenyl)-3-(2-ethoxy-4-methyl-5-benzylaminophenyl)-5/6-carboxyphthalide according to claim 6.

* * * * *